US010406214B2

(12) United States Patent
Kraus

(10) Patent No.: US 10,406,214 B2
(45) Date of Patent: Sep. 10, 2019

(54) PROPIONYL-COA CARBOXYLASE COMPOSITIONS AND USES THEREOF

(71) Applicant: THE REGENTS OF THE UNIVERSITY OF COLORADO, A BODY CORPORATE, Denver, CO (US)

(72) Inventor: Jan P. Kraus, Littleton, CO (US)

(73) Assignee: THE REGENTS OF THE UNIVERSITY OF COLORADO, A BODY CORPORATE, Denver, CO (US)

(*) Notice: Subject to any disclaimer, the term of this patent is extended or adjusted under 35 U.S.C. 154(b) by 0 days.

(21) Appl. No.: 15/571,640

(22) PCT Filed: May 3, 2016

(86) PCT No.: PCT/US2016/030504
§ 371 (c)(1),
(2) Date: Nov. 3, 2017

(87) PCT Pub. No.: WO2016/179138
PCT Pub. Date: Nov. 10, 2016

(65) Prior Publication Data
US 2018/0140688 A1 May 24, 2018

Related U.S. Application Data

(60) Provisional application No. 62/156,296, filed on May 3, 2015.

(51) Int. Cl.
A61K 38/51 (2006.01)
G01N 33/53 (2006.01)
C12Q 1/68 (2018.01)
C12N 9/10 (2006.01)
C07K 14/47 (2006.01)
A61P 43/00 (2006.01)
C12N 15/52 (2006.01)

(52) U.S. Cl.
CPC .............. A61K 38/51 (2013.01); A61P 43/00 (2018.01); C07K 14/47 (2013.01); C12N 9/10 (2013.01); C12N 15/52 (2013.01); C12Q 1/68 (2013.01); G01N 33/53 (2013.01); Y02A 50/473 (2018.01)

(58) Field of Classification Search
CPC ......... A61K 38/51; A61P 43/00; C07K 14/47; Y02A 50/473; C12N 15/52; C12N 9/10; C12Q 1/68; G01N 33/53
See application file for complete search history.

(56) References Cited

U.S. PATENT DOCUMENTS 8,039,587 B2 * 10/2011 Khan .................... A61K 48/005
530/350

FOREIGN PATENT DOCUMENTS

WO WO 03/087768 A2 * 10/2003
WO 2012174452 A1 12/2012

OTHER PUBLICATIONS

Broun et al., Catalytic plasticity of fatty acid modification enzymes underlying chemical diversity of plant lipids. Science, 1998, vol. 282: 1315-1317. (Year: 1998).*
Chloupkova et al., Propionic acidemia: analysis of mutant propionyl-CoA carboxylase enzymes expressed in *Escherichia coli*. Hum. Muta., 2002, vol. 19: 629-640. (Year: 2002).*
Devos et al., Practical limits of function prediction. Proteins: Structure, Function, and Genetics. 2000, vol. 41: 98-107. (Year: 2000).*
Muro et al., Effect of PCCB gene mutations on the heteromeric and homeric assembly of propionyl-CoA carboxylase. Mol. Gen. Metabol., 2001, vol. 74: 476-483. (Year: 2001).*
Seffernick et al., Melamine deaminase and Atrazine chlorohydrolase: 98 percent identical but functionally different. J. Bacteriol., 2001, vol. 183 (8): 2405-2410. (Year: 2001).*
Stankovics et al., Cloning of functional alpha propionyl CoA carboxylase and correction of enzyme deficiency in pccA fibroblasts. Am. J. Hum. Genet., 1993, vol. 52: 144-151. (Year: 1993).*
Veronesse F.M., PEGylated protein drugs: Basic science and clinical applications. Milestones in Drug Therapy MDT, 2009, pp. 1-289. (Year: 2009).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Carrillo-Carrasco, N. & Venditti, C. (2012) Propionic Acidemia, Gene Reviews.
Saudubray, J. M., Ogier, H., Bonnefont, J. P., Munnich, A., Lombes, A., Herve, F., Mitchel, G., The, B. P., Specola, N., Parvy, P. & et al. (1989) Clinical approach to inherited metabolic diseases in the neonatal period: a 20-year survey, J Inherit Metab Dis. 12, 25-41.
Chace, D. H., DiPerna, J. C., Kalas, T. A., Johnson, R. W. & Naylor, E. W. (2001) Rapid Diagnosis of Methylmalonic and Propionic Acidemias: Quantitative Tandem Mass Spectrometric Analysis of Propionylcarnitine in Filter-Paper Blood Specimens Obtained from Newborns. , Clinical Chemistry. 47, 2040-2044.
Ravn, K., Chloupkova, M., Christensen, E., Brandt, N. J., Simonsen, H., Kraus, J. P., Nielsen, I. M., Skovby, F. & Schwartz, M. (2000) High incidence of propionic acidemia in greenland is due to a prevalent mutation, 1540insCCC, in the gene for the beta-subunit of propionyl CoA carboxylase, Am J Hum Genet. 67, 203-6.
Menkes, J. H. (1966) Idiopathic hyperglycinemia: isolation and identification of three previously undescribed urinary ketones, The Journal of pediatrics. 69, 413-21.

(Continued)

Primary Examiner — Ganapathirama Raghu
(74) Attorney, Agent, or Firm — DT Ward, PC; Donna T. Ward; Anna E. Stanford

(57) ABSTRACT

This invention provides compositions of human propionyl-CoA carboxylase (PCC) and pharmaceutical compositions of human PCC and methods for treating conditions such as propionic acidemia (PA), propionic aciduria, propionyl-CoA carboxylase deficiency and ketotic glycinemia.

10 Claims, 3 Drawing Sheets
Specification includes a Sequence Listing.

(56) References Cited

OTHER PUBLICATIONS

Coude, F. X., Sweetman, L. & Nyhan, W. L. (1979) Inhibition by propionyl-coenzyme A of N-acetylglutamate synthetase in rat liver mitochondria. A possible explanation for hyperammonemia in propionic and methylmalonic acidemia, Journal of Clinical Investigation. 64, 1544-51.
Stewart, P. M. & Walser, M. (1980) Failure of the normal ureagenic response to amino acids in organic acid-loaded rats. Proposed mechanism for the hyperammonemia of propionic and methylmalonic acidemia, Journal of Clinical Investigation. 66, 484-92.
Fenton, W. A., Gravel, R. A. & Rosenblatt, D. S. (2001) Disorders of propionate and methylmalonate metabolism in The Metabolic and Molecular Bases of Inherited Disease (Scriver, C. R., Beaudet, A. L., Sly, W. S. & Valle, D., eds) pp. 2165-2204, McGraw-Hill, Inc., New York.
Wolf, B., Hsia, Y. E., Sweetman, L., Gravel, R., Harris, D. J. & Nyhan, W. L. (1981) Propionic acidemia: a clinical update, Journal of Pediatrics. 99, 835-46.
Chloupkova, M., Ravn, K., Schwartz, M. & Kraus, J. P. (2000) Changes in the carboxyl terminus of the beta subunit of human propionyl-CoA carboxylase affect the oligomer assembly and catalysis: expression and characterization of seven patient-derived mutant forms of PCC in *Escherichia coli*, Mol Genet Metab. 71, 623-32.
Gravel, R. A., Lam, K. F., Mahuran, D. & Kronis, A. (1980) Purification of human liver propionyl-CoA carboxylase by carbon tetrachloride extraction and monomeric avidin affinity chromatography, Archives of Biochemistry & Biophysics. 201, 669-73.
Kalousek, F., Darigo, M. D. & Rosenberg, L. E. (1980) Isolation and characterization of propionyl-CoA carboxylase from normal human liver. Evidence for a protomeric tetramer of nonidentical subunits, Journal of Biological Chemistry. 255, 60-5.
Lamhonwah, A. M., Barankiewicz, T. J., Willard, H. F., Mahuran, D. J., Quan, F. & Gravel, R. A. (1986) Isolation of cDNA clones coding for the alpha and beta chains of human propionyl-CoA carboxylase: chromosomal assignments and DNA polymorphisms associated with PCCA and PCCB genes, Proceedings of the National Academy of Sciences of the United States of America. 83, 4864-8.
Kraus, J. P., Williamson, C. L., Firgaira, F. A., Yang-Feng, T. L., Munke, M., Francke, U. & Rosenberg, L. E. (1986) Cloning and screening with nanogram amounts of immunopurified mRNAs: cDNA cloning and chromosomal mapping of cystathionine beta-synthase and the beta subunit of propionyl-CoA carboxylase, Proceedings of the National Academy of Sciences of the United States of America. 83, 2047-51.
Kraus, J. P., Firgaira, F., Novotny, J., Kalousek, F., Williams, K. R., Williamson, C., Ohura, T. & Rosenberg, L. E. (1986) Coding sequence of the precursor of the beta subunit of rat propionyl-CoA carboxylase, Proceedings of the National Academy of Sciences of the United States of America. 83, 8049-53.
Lamhonwah, A. M., Mahuran, D. & Gravel, R. A. (1989) Human mitochondrial propionyl-CoA carboxylase: localization of the N-terminus of the pro- and mature alpha chains in the deduced primary sequence of a full-length cDNA, Nucleic Acids Research. 17, 4396.
Lamhonwah, A. M., Leclerc, D., Loyer, M., Clarizio, R. & Gravel, R. A. (1994) Correction of the metabolic defect in propionic acidemia fibroblasts by microinjection of a full-length cDNA or RNA transcript encoding the propionyl-CoA carboxylase beta subunit, Genomics. 19, 500-5.
Ohura, T., Narisawa, K. & Tada, K. (1993) Propionic acidaemia: sequence analysis of mutant mRNAs from Japanese beta subunit-deficient patients, J Inherit Metab Dis. 16, 863-7.
Browner, M. F., Taroni, F., Sztul, E. & Rosenberg, L. E. (1989) Sequence analysis, biogenesis, and mitochondrial import of the alpha-subunit of rat liver propionyl-CoA carboxylase [published erratum appears in J Biol Chem Mar. 5, 1991;266(7):4660], Journal of Biological Chemistry. 264, 12680-5.
Lamhonwah, A. M., Quan, F. & Gravel, R. A. (1987) Sequence homology around the biotin-binding site of human propionyl-CoA carboxylase and pyruvate carboxylase, Archives of Biochemistry & Biophysics. 254, 631-6.
Leon-Del-Rio, A. & Gravel, R. A. (1994) Sequence requirements for the biotinylation of carboxyl-terminal fragments of human propionyl-CoA carboxylase alpha subunit expressed in *Escherichia coli*, Journal of Biological Chemistry. 269, 22964-8.
Kelson, T. L., Ohura, T. & Kraus, J. P. (1996) Chaperonin-mediated assembly of wild-type and mutant subunits of human propionyl-CoA carboxylase expressed in *Escherichia coli*, Human Molecular Genetics. 5, 331-337.
Fang et al., 2013 PLOS ONE 8(3):e57318.
Ruoslahti et al., 2009 J Cell Biology 188(6):759-68.
Foged & Nielsen, 2008 Expert Opin. Drug Deliv. 5(1):105-17.
Treat et al., 2012 ACS Macro Lett. 1(1):100-04.
Jiang et al., 2005 J Biol.Chem. 280(30):27719-27.
International Search Report dated Aug. 6, 2016 received in corresponding PCT Application No. PCT/US2016/030504.
Communication pursuant to Article 94(3) EPC dated Feb. 19, 2019 in corresponding European Application No. 16722994.7 entitled "Propionyl-CoA Carboxylase Compositions and Uses Thereof".
Maja Chloupkova et al: "Changes in the Carboxyl Terminus of the [beta] Subunit of Human Propionyl-CoA carboxylase Affect the Oligomer Assembly and Catalysis: Expression and Characterization of Seven Patient-Derived Mutant Forms of PCC in *Escherichia coli*", Molecular Genetics and Metabolism, vol. 71, No. 4, Dec. 1, 2000 (Dec. 1, 2000), pp. 623-632. \*\*Prev Cited—Not Provided\*\*.
T. Miyazaki et al: "Fatal Propionic Acidemia in Mice Lacking Propionyl-CoA Carboxylase and Its Rescue by Postnatal, Liver-specific Supplementation via a Transgene", Journal of Biological Chemistry, vol. 276, No. 38, Sep. 21, 2001 (Sep. 21, 2001), pp. 35995-35999. \*\*Prev Cited—Not Provided\*\*.
Israel Office Action received Apr. 10, 2019 in corresponding Israel Application No. 255053 entitled "Propionyl-CoA Carboxylase Compositions and Uses Thereof".
Maja Chloupkova et al: "Changes in the Carboxyl Terminus of the [beta] Subunit of Human Propionyl-CoA Carboxylase Affect the Oligomer Assembly and Catalysis: Expression and Characterization of Seven Patient-Derived Mutant Forms of PCC in *Escherichia coli*", Molecular Genetics and Metabolism, vol. 71, No. 4, Dec. 1, 2000 (Dec. 1, 2000), pp. 623-632.
T. Miyazaki et al: "Fatal Propionic Acidemia in Mice Lacking Propionyl-CoA Carboxylase and Its Rescue by Postnatal, Liver-specific Supplementation via a Transgene", Journal of Biological Chemistry, vol. 276, No. 38, Sep. 21, 2001 (Sep. 21, 2001), pp. 35995-35999.

\* cited by examiner

Figure 1 SDS-PAGE gel of purified PCC

Figure 2 Two patient fibroblast cell lines (3380 and 3383) were incubated with or without 1 µM PCC alone or attached to the TAT peptide for 1 hour at 37°C. The cells were then harvested, extensively washed and tested for PCC activity. 3380 contains a homozygous PCCA mutation and 3383 contains a homozygous PCCB mutation.

Figure 3 An overlay of green fluorescence of the FITC-TAT-PCC, mitochondria stain Mitotracker Red and DAPI (blue) stained nuclei. The cells used were from PA patient 3380 also shown in blue in Fig.2.

PROPIONYL-COA CARBOXYLASE COMPOSITIONS AND USES THEREOF

CROSS REFERENCE TO RELATED APPLICATIONS

This application is a 35 U.S.C. § 371 U.S. National Stage Entry of International Application No. PCT/US2016/030504 filed May 3, 2016, which claims the benefit of U.S. Provisional Patent Application No. 62/156,296, entitled PROPIONYL-COA CARBOXYLASE COMPOSITIONS AND USES THEREOF, filed May 3, 2015; the contents of which are herein incorporated by reference in its entirety.

REFERENCE TO SEQUENCE LISTING

The instant application contains a Sequence Listing which has been submitted electronically in ASCII format and is hereby incorporated by reference in its entirety. Said ASCII copy, created on Nov. 3, 2017 is named 20891500US371_SL.txt and is 22,990 bytes in size.

FIELD OF THE INVENTION

The present invention relates generally to compositions of human propionyl-CoA carboxylase and methods for ameliorating deficits and deficiencies thereof including treating a spectrum of conditions such as propionic acidemia (PA), propionic aciduria, propionyl-CoA carboxylase deficiency and ketotic glycinemia.

BACKGROUND OF THE INVENTION

The spectrum of propionic acidemia (PA) ranges from neonatal-onset to late-onset disease. Neonatal-onset PA, the most common form, is characterized by poor feeding, vomiting, and somnolence in the first days of life in a previously healthy infant, followed by lethargy, seizures, coma, and death. It is frequently accompanied by metabolic acidosis with anion gap, ketonuria, hypoglycemia, hyperammonemia, and cytopenias. Late-onset PA includes developmental regression, chronic vomiting, protein intolerance, failure to thrive, hypotonia, and occasionally basal ganglia infarction (resulting in dystonia and choreoathetosis) and cardiomyopathy (Carrillo-Carrasco & Venditti, 2012 *Gene Reviews*). The incidence of PA has been estimated to be similar to that reported for methylmalonic acidemia, in the range of 1:35,000-1:70,000 (Saudubray et al., 1989 *J Inherit Metab Dis.* 12:25-41; Chace et al., 2001 *Clinical Chemistry* 47:2040-44). Propionic acidemia can be caused by mutations in one or both of genes encoding propionyl-CoA carboxylase (PCC); i.e., subunits PCCA or PCCB. PA can also result from a decrease in PCC activity from a lack of co-enzymes such as biotin. A collaborative report with the inventors found the incidence of PA carriers to be ~5% in the Inuit population of Greenland, which is very high compared with those of most other autosomal recessive diseases (Ravn et al., 2000 *Am J Hum Genet.* 67:203-6). Biochemically, patients with this disorder present with elevated levels of propionyl CoA, propionic acid, methylcitrate, beta-hydroxypropionate, propionylglycine, tiglic acid, and ketones. Ketones such as butanone may also be found in the urine (Menkes et al., 1966 *The Journal of pediatrics.* 69:413-21). Hyperammonemia originates secondarily from carbamoyl phosphate synthetase inhibition (Coude et al., 1979 *Journal of Clinical Investigation.* 64:1544-51; Stewart & Walser, 1980 *Journal of Clinical Investigation.* 66:484-92). Ketoacidotic episodes are frequently life threatening and ⅓ of affected neonates die within the first few weeks of life (Fenton et al., 2001 *Disorders of propionate and methylmalonate metabolism in The Metabolic and Molecular Bases of Inherited Disease* (Scriver, C. R., Beaudet, A. L., Sly, W. S. & Valle, D., eds) pp. 2165-2204, McGraw-Hill, Inc., New York). The condition can be treated by severely restricting protein intake; however, management of such patients is often difficult (Wolf et al., 1981 *Journal of Pediatrics.* 99:835-46). The inventors have previously demonstrated that human PCC is an $\alpha_6\beta_6$ heterododecamer (Chloupkova et al., 2000 *Mol Genet Metab.* 71:623-32). The 72 kDa α subunit and the 56 kDa β subunit (Gravel et al., 1980 *Archives of Biochemistry & Biophysics.* 201:669-73; Kalousek et al., 1980 *Journal of Biological Chemistry.* 255:60-5) are encoded by separate genes designated, PCCA, found on chromosome 13 (Lamhonwah et al., 1986 *Proc. Nat. Acad. Sci.* 83:4864-8), and PCCB, found on chromosome 3 (Kraus et al., 1986 *Proc. Nat. Acad. Sci.* 83:2047-51), respectively. Both corresponding cDNAs have been sequenced (Kraus et al., 1986 *Proc. Nat. Acad. Sci.* 83:8049-53; Lamhonwah et al., 1989 *Nucleic Acids Research.* 17:4396; Lamhonwah et al., 1994 *Genomics.* 19:500-; Ohura et al., 1993 *J Inherit Metab Dis.* 16:863-7). The subunits are synthesized as longer precursors, imported into the mitochondrion, cleaved and assembled (Kraus et al., 1986 *Proc. Nat. Acad. Sci.* 83:8049-53; Browner et al., 1989 *Journal of Biological Chemistry.* 264:12680-5). The alpha subunit contains the sequence that accepts biotin (Kalousek et al., 1980 *Journal of Biological Chemistry.* 255:60-5; Lamhonwah et al., 1987 *Archives of Biochemistry & Biophysics.* 254:631-6; Leon-Del-Rio & Gravel 1994 *Journal of Biological Chemistry.* 269:22964-8); it also binds $CO_2$, $Mg^{2+}$, ATP, and can be up regulated by binding $K^+$ (Kalousek et al., 1980 *Journal of Biological Chemistry.* 255: 60-5). The beta □subunit binds propionyl-CoA (Fenton et al., 2001 *Disorders of propionate and methylmalonate metabolism in The Metabolic and Molecular Bases of Inherited Disease* (Scriver, C. R., Beaudet, A. L., Sly, W. S. & Valle, D., eds) pp. 2165-2204, McGraw-Hill, Inc., New York). Mutations in either gene result in PA. To date, 81 and 86 mutations have been identified in the PCCA and PCCB genes from propionic acidemia patients, respectively (a public continuously updated list of all reported PCC mutations can be found at the Kraus lab webpage at the University of Colorado-Denver Medical School).

Currently, there is no cure for PA or other PCC-deficiency related conditions and current treatment provides only partial alleviation of symptoms. Enzyme therapy is a therapeutic approach in which the deficient enzyme is replaced by recombinant active protein. The inventors aim to develop a way to deliver active PCC to afflicted patients. However, the ability to specifically deliver PCC to the mitochondria presents a challenge. Thus there remains a need in this art to develop compositions, including pharmaceutical compositions, and methods for delivering active PCC to the intracellular mitochondrial site of its activity to ameliorate deficits and deficiencies thereof.

SUMMARY OF THE INVENTION

It is against the above background that the present invention provides certain advantages and advancements over the prior art.

This invention provides compositions, including pharmaceutical compositions, and methods for delivering active PCC to the intracellular mitochondrial site of its activity to ameliorate deficits and deficiencies thereof.

In one embodiment of the invention, the disease propionic acidemia (PA), due to propionyl-CoA carboxylase (PCC) deficiency is addressed. PCC is a biotin-dependent, mitochondrial matrix enzyme involved in organic acid metabolism in humans. PA is a devastating disease with one third of affected infants dying in early infancy. The inventors are currently systematically studying the biochemistry and molecular genetics of this disorder. The invention works to directly address the issue of treatment of this disorder or other PCC-deficiency related conditions, and the results shown here using cell-penetrating proteins, such as TAT, indicate that import of assembled PCC or the individual PCC subunits into cells including the mitochondria to correct the propionyl-CoA carboxylase enzyme deficiency is possible.

In various aspects of the invention provides a method for providing isolated human propionyl-CoA carboxylase (PCC) to a cell having a deficiency thereof wherein the PCC comprises one or both of an isolated propionyl-CoA carboxylase, alpha chain protein (PCCA) comprising the amino acid sequence of SEQ ID NO:2, and/or an isolated propionyl-CoA carboxylase, beta chain protein (PCCB) comprising the amino acid sequence of SEQ ID NO:4, wherein the method comprises the steps of contacting said cell with a preparation of the isolated human PCC at a concentration sufficient for the cell to take up a therapeutically effective amount of PCC, wherein the PCC deficiency in the cell is alleviated thereby.

In a further aspect, the invention provides a method for treating PCC deficiency in an individual in need thereof, comprising administering a therapeutically effective amount of a pharmaceutical composition of isolated human PCC to the individual in need thereof, wherein the isolated human PCC comprises one or both of an isolated propionyl-CoA carboxylase, alpha chain protein (PCCA) comprising the amino acid sequence of SEQ ID NO:2, and/or an isolated propionyl-CoA carboxylase, beta chain protein (PCCB) comprising the amino acid sequence of SEQ ID NO:4.

In yet another aspect, the invention provides pharmaceutical composition comprising a therapeutically effective amount of isolated human PCC wherein the PCC comprises one or both of an isolated propionyl-CoA carboxylase, alpha chain protein (PCCA) comprising the amino acid sequence of SEQ ID NO:2, and/or an isolated propionyl-CoA carboxylase, beta chain protein (PCCB) comprising the amino acid sequence of SEQ ID NO:4, and a pharmaceutically acceptable carrier, diluent or excipient.

In some embodiments, the pharmaceutical composition is administered by intravenous injection, subcutaneous injection, or intraperitoneal injection. The pharmaceutical composition may comprise an amount of PCC protein wherein 0.1 mg/kg-20 mg/kg is administered to an individual in need thereof.

In another embodiment, the invention provides a method for treating or ameliorating a disease, disorder, or condition, associated with elevated propionyl CoA, propionic acid, methylcitrate, beta-hydroxy-propionate, propionylglycine, tiglic acid, and ketones comprising administering to an individual in need thereof a pharmaceutically effective amount of a pharmaceutical composition of PCC. In one embodiment, the disease, disorder, or condition associated with elevated propionyl CoA, propionic acid, methylcitrate, beta-hydroxy-propionate, propionylglycine, tiglic acid, and ketones is poor feeding, vomiting, and somnolence, lethargy, seizures, coma, metabolic acidosis, anion gap, ketonuria, hypoglycemia, hyperammonemia, cytopenias, developmental regression, chronic vomiting, protein intolerance, failure to thrive, hypotonia, basal ganglia infarction, dystonia, choreoathetosis, and cardiomyopathy.

In certain embodiments, the invention provides a composition of matter comprising one or both of an isolated propionyl-CoA carboxylase, alpha chain protein (PCCA) comprising the amino acid sequence of SEQ ID NO:2, and/or an isolated propionyl-CoA carboxylase, beta chain protein (PCCB) comprising the amino acid sequence of SEQ ID NO:4.

In other aspects the PCCA protein and/or PCCB protein comprises a mitochondrial leader sequence. In yet other aspects the PCCA protein and/or PCCB protein lack a mitochondrial leader sequence. In various embodiments the PCCA protein and/or PCCB proteins are genetically engineered proteins or variants thereof.

In another embodiment the PCCA protein and/or PCCB protein is covalently linked to one or a plurality of cell penetrating proteins, a non-limiting example of such a cell penetration protein is trans-activating transcriptional activator (TAT) or a tissue specific variant thereof. In some embodiments the cell-penetrating protein is chemically added post-translation of the PCCA or PCCB peptide.

In certain embodiments, the PCCA and/or PCCB proteins are produced recombinantly. The PCCA and/or PCCB proteins may be produced in prokaryotic or eukaryotic cells, more specifically yeast, mammalian or *E. coli*.

In other embodiments, the PCCA and/or PCCB proteins are covalently linked to one or a plurality of polyethylene glycol molecules.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings.

Figure 1:
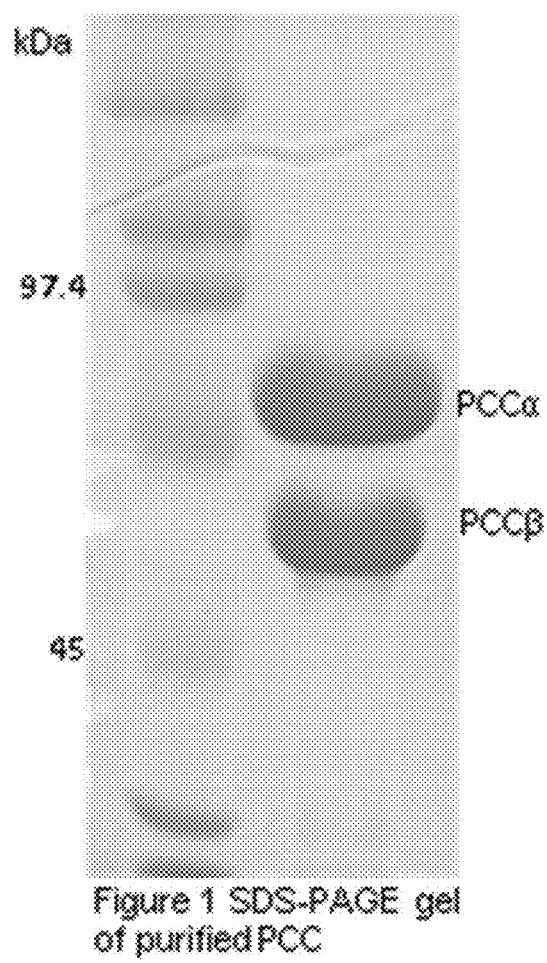
FIG. 1 shows an SDS-PAGE gel of purified recombinant human propionyl-CoA carboxylase.
Figure 2:
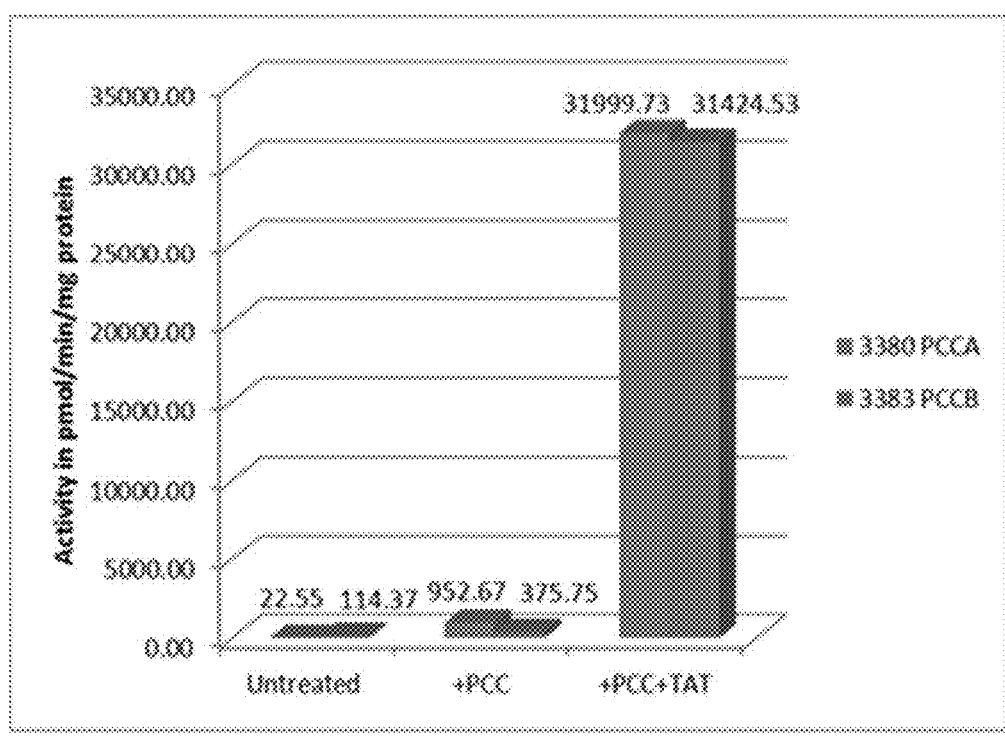
FIG. 2 shows the activity of propionyl-CoA carboxylase with or without the trans-activating transcriptional activator (TAT) peptide in two PA patient-derived human fibroblast cell lines.
Figure 3:
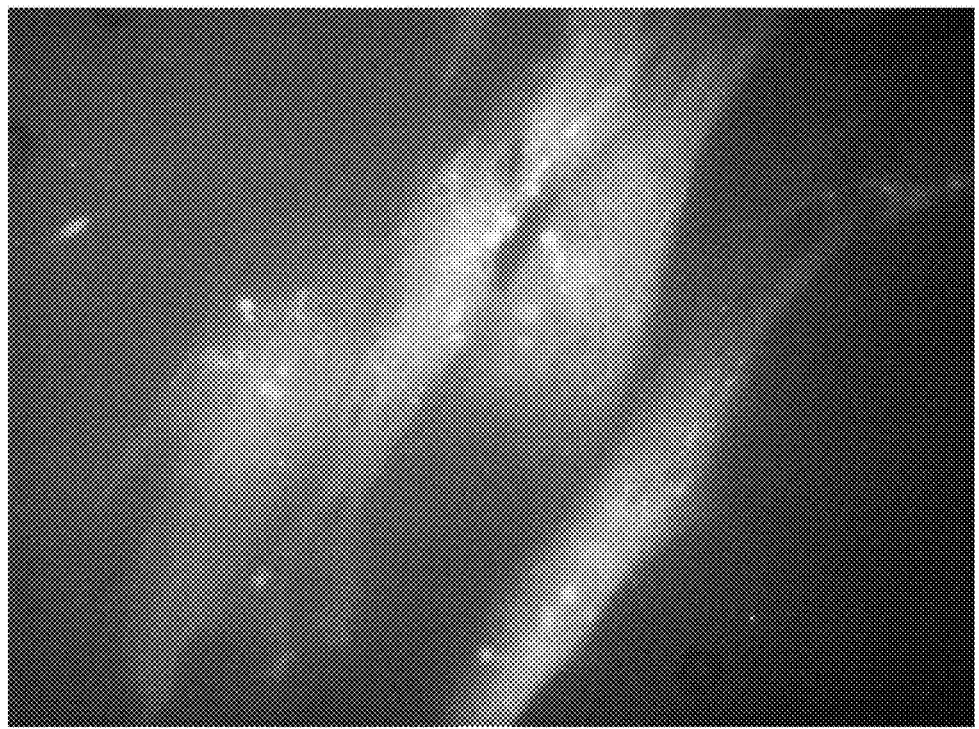
FIG. 3 shows the staining of the FITC-TAT-PCC protein in a PA patient-derived human fibroblast cell line demonstrating internalization of the TAT-PCC protein with some co-localization to the mitochondria.

Skilled artisans will appreciate that elements in the figures are illustrated for simplicity and clarity and have not necessarily been drawn to scale. For example, the dimensions of some of the elements in the figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Provided herein are compositions, specifically pharmaceutical compositions, and methods for treating patients with propionic academia (PA) or other PCC-deficiency related conditions, for example, by enzyme therapy. The spectrum of PA (also referred to as: propionyl-CoA carboxylase deficiency, PCC deficiency, ketotic glycinemia, hyperglycinemia with ketoacidosis and leukopenia, or ketotic hyperglycinemia), ranges from neonatal-onset to late-onset disease. Neonatal-onset PA, the most common form, is characterized by poor feeding, vomiting, and somnolence in the first days of life in a previously healthy infant, followed by lethargy, seizures, coma, and death. It is frequently accompanied by metabolic acidosis with anion gap, ketonuria, hypoglycemia, hyperammonemia, and cytopenias. Late-onset PA includes developmental regression, chronic vomiting, protein intolerance, failure to thrive, hypotonia, and occasionally basal ganglia infarction (resulting in dystonia and choreoathetosis) and cardiomyopathy. Accordingly, in one embodiment, the method of the present invention provides a method for treating or ameliorating a disease, disorder, or condition, associated with elevated propionyl CoA, propionic acid, methylcitrate, beta-hydroxy-propionate, propionylglycine, tiglic acid, and ketones comprising administering to an individual in need thereof a pharmaceutically effective amount of a composition comprising PCC proteins. The term, "disease" refers to any deviation from the normal health of a patient and includes a state when disease symptoms are present, as well as conditions in which a deviation (e.g., in non-limiting examples including infection, gene mutation, and genetic defect, etc.) has occurred, but symptoms are not yet manifested (e.g., a predisease condition).

More specifically, a therapeutic composition as described herein, when administered to a patient by the method of the present invention, preferably produces a result which can include alleviation of the disease (e.g., reduction of at least one symptom or clinical manifestation of the disease), elimination of the disease, alleviation of a secondary disease resulting from the occurrence of a primary disease, or prevention of the disease.

The nucleic acid sequences encoding human PCC and the amino acid sequences encoded thereby are shown in Table 1. The DNA sequence for propionyl Coenzyme A carboxylase, alpha protein (PCCA) is represented herein as SEQ ID NO:1, and the amino acid sequence for full-length human PCCA, having 702 amino acid residues, is SEQ ID NO:2. The DNA sequence for propionyl Coenzyme A carboxylase, beta protein (PCCB) is represented herein as SEQ ID NO:3, and the amino acid sequence for full-length human PCCB, having 539 amino acid residues, is SEQ ID NO:4. The nucleic acid sequence of the genomic DNA encoding PCCA and PCCB is also publicly available through sequence databases such as Genbank and at University of Colorado-Denver webpage under Kraus Lab.

TABLE 1

| Nucleic acid and protein sequences for human PCC | |
|---|---|
| PCCA<br>Nucleotide<br>NM_000282<br>X14608<br>propionly-CoA<br>carboxylase<br>alpha chain,<br>mitochondrial<br>isoform a<br>precursor<br>SEQ ID NO: 1 | ggcatcgggtttctggctcgtgatttgccggagctcctgcgctcccttc<br>tccaccccctccggctgtgtgagaggtcagcagaggggcggtctgcgggg<br>acaacaatggcggggttctgggtcgggacagcaccgctggtcgctgccgg<br>acggcgtgggcggtggccgccgcagcagctgatgctgagcgcgcgctgc<br>ggaccctgaagcatgttctgtactattcaagacagtgcttaatggtgtcc<br>cgtaatcttggttcagtgggatatgatcctaatgaaaaaacttttgataa<br>aattcttgttgctaatagaggagaaattgcatgtcgggttattagaactt<br>gcaagaagatgggcattaagacagttgccatccacagtgatgttgatgct<br>agttctgttcatgtgaaaatggcggatgaggctgtctgtgttggcccagc<br>tcccaccagtaaaagctacctcaacatggatgccatcatggaagccatta<br>agaaaaccagggcccaagctgtacatccaggttatggattcctttcagaa<br>aacaaagaatttgccagatgtttggcagcagaagatgtcgttttcattgg<br>acctgacacacatgctattcaagccatgggcgacaagattgaaagcaaat<br>tattagctaagaaagcagaggttaatacaatccctggctttgatggagta<br>gtcaaggatgcagaagaagctgtcagaattgcaagggaaattggctaccc<br>tgtcatgatcaaggcctcagcaggtggtggtgggaaaggcatgcgcattg<br>cttgggatgatgaagagaccagggatggttttagattgtcatctcaagaa<br>gctgcttctagttttggcgatgatagactactaatagaaaaatttattga<br>taatcctcgtcatatagaaatccaggttctaggtgataaacatgggaatg<br>ctttatggcttaatgaaagagagtgctcaattcagagaagaaatcagaag<br>gtggtggaggaagcaccaagcattttttttggatgcggagactcgaagagc<br>gatgggagaacaagctgtagctcttgccagagcagtaaaatattcctctg<br>ctgggaccgtggagttccttgtggactctaagaagaattttttatttcttg<br>gaaatgaatacaagactccaggttgagcatcctgtcacagaatgcattac<br>tggcctggacctagtccaggaaatgatccgtgttgctaagggctaccctc<br>tcaggcacaaacaagctgatattcgcatcaacggctgggcagttgaatgt<br>cgggtttatgctgaggaccccctacaagtcttttggtttaccatctattgg<br>gagattgtctcagtaccaagaaccgttacatctacctggtgtccgagtgg<br>acagtggcatccaaccaggaagtgatattagcatttattatgatcctatg<br>atttcaaaactaatcacatatggctctgatagaactgaggcactgaagag<br>aatggcagatgcactggataactatgttattcgaggtgttacacataata<br>ttgcattacttcgagaggtgataatcaactcacgcttttgtaaaaggagac<br>atcagcactaaatttctctccgatgtgtatcctgatggcttcaaaggaca<br>catgctaaccaagagtgagaagaaccagttattggcaatagcatcatcat<br>tgtttgtggcattccagttaagagcacaacattttcaagaaaattcaaga<br>atgcctgttattaaaccagacatagccaactgggagctctcagtaaaatt<br>gcatgataaagttcataccgtagtagcatcaaacaatgggtcagtgttct<br>cggtggaagttgatgggtcgaaactaaatgtgaccagcacgtggaacctg<br>gcttcgcccttattgtctgtcagcgttgatggcactcagaggactgtcca<br>gtgtctttctcgagaagcaggtggaaacatgagcattcagtttcttgta<br>cagtgtacaaggtgaatatcttaaccagacttgccgcagaattgaacaaa<br>tttatgctggaaaaagtgactgaggacacaagcagtgttctgcgttcccc<br>gatgcccggagtggtggtggccgtctctgtcaagcctggagacgcggtag |

TABLE 1-continued

Nucleic acid and protein sequences for human PCC

|  |  |
|---|---|
|  | cagaaggtcaagaaatttgtgtgattgaagccatgaaaatgcagaatagt<br>atgacagctgggaaaactggcacggtgaaatctgtgcactgtcaagctgg<br>agacacagttgggagaaggggatctgctcgtggagctggaatgaaggattt<br>ataaccttcagtcatcacccaatttaattagccatttgcatgatgctttt<br>cacacacaattgattcaagcattatacaggaacacccctgtgcagctacg<br>tttacgtcgtcatttattccacagagtcaagaccaatattctgccaaaaa<br>atcaccaatggaaattttcattgatataaatacttgtacatatgattgt<br>acttctgctgtgagattccctagtgtcaaaattaaatcaataaaactgag<br>catttgtctaaataaaaaaaaaaaaaa |
| PCCA<br>Protein<br>NP_000273<br>P05165<br>propionyl-CoA<br>carboxylase<br>alpha chain,<br>mitochondrial<br>isoform a<br>precursor<br>SEQ ID NO: 2 | MAGFWVGTAPLVAAGRRGRWPPQQLMLSAALRTLKHVLYYSRQC<br>LMVSRNLGSVGYDPNEKTEDKILVANRGEIACRVIRICKKMGIKTVAIHSDVDASSVH<br>VKMADEAVCVGPAPTSKSYLNMDAIMEAIKKTRAQAVHPGYGELSENKEFARCLAAED<br>VVFIGPDTHAIQAMGDKIESKLLAKKAEVNTIPGEDGVVKDAEEAVRIAREIGYPVMI<br>KASAGGGKGMRIAWDDEETRDGFRLSSQEAASSFGDDRLLIEKFIDNPRHIEIQVLG<br>DKHGNALWLNERECSIQRRNQKVVEEAPSIFLDAETRRAMGEQAVALARAVKYSSAGT<br>VEFLVDSKKNFYFLEMNTRLQVEHPVTECITGLDLVQEMIRVAKGYPLRHKQADIRIN<br>GWAVECRVYAEDPYKSFGLPSIGRLSQYQEPLHLPGVRVDSGIQPGSDISIYYDPMIS<br>KLITYGSDRTEALKRMADALDNYVIRGVIHNIALLREVIINSRFVKGDISTKELSDVY<br>PDGFKGHMLIKSEKNQLLAIASSLEVAFQLRAQHFQENSRMPVIKPDIANWELSVKLH<br>DKVHTVVASNNGSVFSVEVDGSKLNVTSTWNLASPLLSVSVDGTQRTVQCLSREAGGN<br>MSIQFLGTVYKVNILTRLAAELNKFMLEKVIEDISSVLRSPMPGVVVAVSVKPGDAVA<br>EGQEICVIEAMKMQNSMTAGKIGTVKSVHCQAGDTVGEGDLLVELE |
| PCCB<br>Nucleotide<br>NM_000532<br>propionyl-CoA<br>carboxylase<br>beta chain,<br>mitochondrial<br>isoform 1<br>precursor<br>SEQ ID NO: 3 | agcacatgcgtactcaggtgcgccggtaggggacgcgccggcacagcaaa<br>aatggcggcggcattacgggtggcggcggtcggggcaaggctcagcgttc<br>tggcgagcggtctccgcgccgcggtccgcagccttgcagccaggccacc<br>tctgttaacgaacgcatcgaaaacaagcgccggaccgcgcgctgctgggagg<br>gggccaacgccgtattgacgcgcagcacaagcgaggaaagctaacagcca<br>gggagaggatcagtctcttgctggaccctggcagctttgttgagagcgac<br>atgtttgtggaacacagatgtgcagattttggaatggctgctgataagaa<br>taagttcctggagacagcgtggtcactggacgaggccgaatcaatggaa<br>gattggtttatgtcttcagtcaggatttttacagtttttggaggcagtctg<br>tcaggagcacatgcccaaaagatctgcaaaatcatggaccaggccataac<br>ggtgggggctccagtgattgggctgaatgactctgggggagcacggatcc<br>aagaaggagtggagtcttggctggctatgcagacatctttctgaggaat<br>gttacggcatccggagtcatccctcagatttctctgatcatgggcccatg<br>tgctggtggggccgtctactcccagccctaacagacttcacgttcatgg<br>taaaggacacctcctacctgttcatcactggcctgatgttgtgaagtct<br>gtcaccaatgaggatgttaccaggaggagctcggtggtgccaagaccca<br>caccaccatgtcaggtgtggcccacagagcttttgaaaatgatgttgatg<br>ccttgtgtaatctccgggatttcttcaactacctgcccctgagcagtcag<br>gacccggctcccgtccgtgagtgccacgatcccagtgaccgtctggttcc<br>tgagcttgacacaattgtccccttttggaatcaaccaaagcctacaacatgg<br>tggacatcatacactctgttgttgatgagcgtgaatttttttgagatcatg<br>cccaattatgccaagaacatcattgttggttttgcaagaatgaatgggag<br>gactgttggaattgttggcaaccaacctaaggtggcctcaggatgcttgg<br>atattaattcatctgtgaaaggggctcgttttgtcagattctgtgatgca<br>ttcaatattccactcatcacttttgttgatgtccctggctttctacctgg<br>cacagcacaggaatacggggggcatcatccggcatggtgccaagcttctct<br>acgcatttgctgaggcaactgtacccaaagtcacagtcatcaccaggaag<br>gcctatggaggtgcctatgatgtcatgagctctaagcacctttgtggtga<br>taccaactatgcctggcccaccgcagagattgcagtcatgggagcaaagg<br>gcgctgtggagatcatcttcaaagggcatgagaatgtggaagctgctcag<br>gcagagtacatcgagaagtttgccaaccctttccctgcagcagtgcgagg<br>gtttgtggatgacatcatccaaccttcttccacacgtgcccgaatctgct<br>gtgacctggatgtcttggccagcaagaaggtacaacgtccttggagaaa<br>catgcaaatattccattgtaaacaaatcaaaggaaaagaaaccaagaact<br>gaattactgtctgcccattcacatcccattcctgccttttgcaatcatga<br>aacctgggaatccaaatagttggataacttagaataactaagtttattaa<br>attctagaaagatctcaaaaaaaa |
| PCCB<br>Protein<br>NP_000523<br>P05166<br>propionyl-CoA<br>carboxylase<br>beta chain,<br>mitochondrial<br>isoform 1<br>precursor<br>SEQ ID NO: 4 | MAAALRVAAVGARLSVLASGLRAAVRSLCSQATSVNERIENKRR<br>TALLGGGQRRIDAQHKRGKLTARERISLLLDPGSFVESDMFVEHRCADFGMAADKNKF<br>PGDSVVTGRGRINGRLVYVFSQDFTVFGGSLSGAHAQKICKIMDQAITVGAPVIGLND<br>SGGARIQEGVESLAGYADIFLRNVTASGVIPQISLIMGPCAGGAVYSPALTDFTFMVK<br>DTSYLFITGPDVVKSVINEDVTQEELGGAKTHITMSGVAHRAFENDVDALCNLRDFFN<br>YLPLSSQDPAPVRECHDPSDRLVPELDTIVPLESTKAYNMVDIIHSVVDEREFFEIMP<br>NYAKNIIVGFARMNGRTVGIVGNQPKVASGCLDINSSVKGARFVRFCDAFNIPLITFV<br>DVPGFLPGTAQEYGGIIRHGAKLLYAFAEATVPKVIVITRKAYGGAYDVMSSKHLCGD<br>TNYAWPTAEIAMMGAKGAVEIIFKGHENVEAAQAEYIEKFANPFPAAVRGFVDDIIQP<br>SSTRARICCDLDVLASKKVQRPWRKHANIPL |

As used herein, an isolated protein or protein in the invention is specifically a version of isolated propionyl-CoA carboxylase, particularly human PCC protein. The inventors have demonstrated that human PCC is an alpha-6:beta-6 heterododecamer (Chloupkova et al., 2000 *Mol Genet Metab.* 71:623-32). The 72 kDa PCC-alpha subunit and the 56 kDa PCC-beta subunit are encoded by separate genes designated, PCCA, and PCCB. The PCC protein of the present invention can include, but is not limited to, purified PCCA and PCCB proteins, chemically cleaved and recombinantly produced PCCA and PCCB proteins, and isolated PCCA and PCCB proteins associated with other proteins. More specifically, an isolated human PCC peptide, according to the present invention, is an PCCA-6:PCCB-6 heterododecamer protein (including a polyprotein or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. An isolated human PCC protein of the present invention can be produced recombinantly in cells, for example bacterial cells. In addition, and by way of example, a "human PCC peptide" refers to a PCC protein (as set forth herein) from a human (*Homo sapiens*) or to a PCC protein that has been otherwise produced from the knowledge of the structure (e.g., sequence) and perhaps the function of a naturally occurring PCC protein from *Homo sapiens*. In other words, a human PCC protein includes biologically active, human PCC protein as described in detail herein. In particular embodiments, the invention provides a PCCA-6:PCCB-6 heterododecamer protein.

A particular chromatographic separation step in the certain embodiments of the methods provided by this invention comprises an ion exchange chromatography column. In one embodiment, the ion exchange chromatography column is an anion exchanger. Various types of anion exchange resins can be used, DEAE-cellulose, DEAE-cellulose DE 52 and DEAE-Sepharose-FF. According to one embodiment, the anion exchange resin is DEAE-Sepharose-FF.

Additional chromatographic steps provided in certain embodiments of the methods of this invention for purifying PCC from a PCC-containing solution include use of an monomeric avidin column. Avidin columns are useful for non-denaturing affinity purification of biotinylated molecules.

Chromatography matrices useful in the method of the invention are materials capable of binding biochemical compounds, preferably proteins, nucleic acids, and/or endotoxins, wherein the affinity of said biochemical compounds to said chromatography matrix is influenced by the ion composition of the surrounding solution (buffer). Controlling the ion composition of said solution allows to use the chromatography materials of the invention either in subtractive mode (PCC passes through said chromatography matrix, at least certain contaminants bind to said chromatography matrix) or, preferably, in adsorptive mode (PCC binds to the chromatography matrix).

In particular embodiments, the method for purification comprises the step of homogenizing host cells, particularly recombinant cells and in certain embodiments, recombinant cells producing mammalian, preferable human, PCC proteins, wherein said recombinant construct encodes a PCC protein that is a naturally occurring or a genetically engineered variant thereof, and particularly wherein said construct has been optimized for recombinant cell expression. In particular embodiments, said recombinant cells are prokaryotic cells, particularly bacterial cells or eukaryotic cells, particularly yeast or mammalian cells. In certain particular embodiments, the bacterial cells are *E. coli* cells and the PCC sequence has been engineered in the recombinant expression construct to be optimized for expression in said cells; a specific embodiment of such a nucleic acid sequence optimized for PCC expression in *E. coli* is set forth in the plasmide pPCCAB of Example 2, which is also described in Kelson et al., 1996 *Human Molecular Genetics.* 5:331-37. In said methods, cells are harvested, e.g. by centrifugation, and optionally stored at −80° C. Homogenization of host cells is performed by disrupting the cells host using physical, chemical or enzymatic means or by a combination thereof. Advantageously, for purification from bacterial sources homogenation is performed by disrupting the cell wall of said bacterial host by sonication. Alternatively or additionally homogenizing is performed by destabilizing the bacterial cell wall of the host by exposure to a cell wall degrading enzyme such as lysozyme.

The methods of the invention can further comprise a clarified PCC homogenate, wherein cell debris is removed from the homogenate by either filtration or centrifugation. In certain embodiments, clarifying is performed by centrifuging the homogenate at an effective rotational speed. The required centrifugation time depends inter alia on the volume of the homogenate, which can be determined empirically to obtain a sufficiently solid pellet. To obtain an essentially cell debris-free clarified homogenate a combination of centrifugation and filtration can be performed on the homogenate.

The term "recombinant cell" as used herein refers to suitable cells (including progeny of such cells) from any species (prokaryotic or eukaryotic) into which has been introduced a recombinant expression construct capable of expressing a nucleic acid encoding PCC peptide, preferably human PCC protein or a genetically engineered variant thereof.

The term, "bacterial cell", as used herein refers to bacteria that produces a mammalian, preferably human, PCC protein inter alia using recombinant genetic methods including progeny of said recombinant cell, wherein said PCC protein is a naturally occurring variant, or a genetically engineered variant thereof.

The term "recombinant expression construct" as used herein refers to a nucleic acid having a nucleotide sequence of a mammalian, preferably human, PCC protein, and sequences sufficient to direct the synthesis of PCC protein in cultures of cells into which the recombinant expression construct is introduced and the progeny thereof.

Methods to measure protein expression levels of the PCC protein according to the invention include, but are not limited to Coomasie blue or silver staining of protein in a separation media, such as gel electrophoresis, Western blotting, immunocytochemistry, other immunologic-based assays; assays based on a property of the protein including but not limited to, enzyme assays, ligand binding or interaction with other protein partners.

In certain aspects, a PCC protein of the present invention comprises an amino acid sequence that is less than 100% identical to SEQ ID NO:2 and SEQ ID NO:4, and in specific embodiments having 90% sequence identity, 91% sequence identity, 92% sequence identity, 93% sequence identity, 94% sequence identity, 95% sequence identity, 96% sequence identity, 97% sequence identity, 98% sequence identity, or 99% sequence identity, to SEQ ID NO:2 and SEQ ID NO:4.

As used herein, unless otherwise specified, reference to a percent (%) identity refers to an evaluation of homology which is performed using a sequence alignment tool or program, including but not limited to (1) a BLAST 2.0 Basic BLAST homology search using blastp for amino acid searches and blastn for nucleic acid searches with standard default parameters, wherein the query sequence is filtered for low complexity regions by default; (2) a BLAST 2 alignment (using the parameters described below); (3) PSI-BLAST with the standard default parameters (Position-Specific Iterated BLAST; (4) and/or Clustal Omega. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using anyone of these programs.

The PCC protein can be linked with a molecule that permits cell entry of the PCC protein, in some embodiments this comprises a cell penetrating peptide. Cell-penetrating peptides are short peptides (typically less than 30 amino acids) that facilitate cellular uptake of various molecules. Cell penetrating peptides are tools for non-invasive cellular import of cargo and have been successfully applied for in vitro and in vivo delivery of therapeutic molecules varying from small chemical molecules, nucleic acids, proteins, peptides, liposomes and particles. A cell penetrating peptide can be linked to a molecule through covalent bonds or non-covalent bonds, and are coupled to the PCC peptides using standard methods of bioconjugation. A non-limiting example of a cell penetrating protein is the HIV-1 trans-activating transcriptional activator (TAT) peptide or its variants (e.g., YGRKKRRQRRR; SEQ ID NO:5; GRKKRRQRRRPQ, SEQ ID NO:6; CFITKALGISYGRKKRRQRRRPPQGSQTHQVSLSKQ SEQ ID NO:20). Some other common cell penetrating peptides include: 1) homeodomain transcription factors such as Antennapedia (RQIKIYFQNRRMKWKK, SEQ ID NO:7), the herpes simplex virus type 1 protein VP22 (DAATATRGRSAASRPTERPRAPARSASRPRRPVD, SEQ ID NO:8), the HIV trans-activating transcriptional activator (YGRKKRRQRRR, SEQ ID NO:5), penetratin (RQIKIWFQNRRMKWKK, SEQ ID NO:9), transportan (GWTLNSAGYLLGKINLKALAALAKKIL, SEQ ID NO:10), 2) ampiphatic proteins such as MPG (GALFLG-FLGAAGSTMGAWSQPKKKRKV, SEQ ID NO:11), Pep-1 (KETVWVETVWVTEWSQPKKKRKV, SEQ ID NO:12), MAP (KALAKALAKALA, SEQ ID NO:13), SAP (VRLP-PPVRLPPPVRLPPP, SEQ ID NO:14), PPTG1 (GLFRALL-RLLRSLWRLLLRA, SEQ ID NO:15); and 3) other peptides such as poly-Arginine sequences (e.g., RRRRRRRR, SEQ ID NO:16), hCT (LGTYTQDFNKTFPQTAIGVGAP, SEQ ID NO:17), SynB (RGGRLSYSRRRFSTSTGR, SEQ ID NO:18), and Pvec (LLIILRRRIRKQAHAHSK, SEQ ID NO:19). Cell penetrating proteins are discussed, for example, in: Fang et al., 2013 PLOS ONE 8(3):e57318; Ruoslahti et al., 2009 *J Cell Biology* 188(6):759-68; Foged & Nielsen, 2008 *Expert Opin. Drug Deliv.* 5(1):105-17; and Treat et al., 2012 *ACS Macro Lett.* 1(1):100-04.

PCC derivatives are included in the scope of the present invention. Examples of PCC derivatives or variants, include, but are not limited to, genetically engineered modifications including nucleic acid and/or amino acid modifications or chemical modifications that, for example, mask potential immunogenic epitopes on the surface of a protein and/or hinder access to the protein for proteolytic enzymes are of interest. Other modifications of interest include those that advantageously alter the physico-chemical properties of the PCC peptide, thus modifying its biodistribution, stability, and solubility without significantly detracting from its potency. Such derivatives may be chemically modified PCC protein compositions in which PCC protein is linked to a polymer. The polymer selected is typically water-soluble so that the protein to which it is attached does not precipitate in an aqueous environment, such as a physiological environment. The polymer may be of any molecular weight, and may be branched or unbranched. Included within the scope of PCC protein polymers is a mixture of polymers. In specific embodiments, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran (such as low molecular weight dextran, of, for example about 6 kDa), cellulose, or other carbohydrate based polymers, poly-(N-vinyl pyrrolidone) polyethylene glycol, propylene glycol homopolymers, a polypropylene oxide/ethylene oxide co-polymer, polyoxyethylatedpolyols (e.g., glycerol), polysalicylic acid, and polyvinyl alcohol. Also encompassed by the invention are bifunctional PEG cross-linking molecules that may be used to prepare covalently attached PCC multimers. One water-soluble polymer for use herein is polyethylene glycol, abbreviated PEG. As used herein, polyethylene glycol is meant to encompass any of the forms of PEG that have been used to derivatize other proteins, such as mono-($C_1$-$C_{10}$) alkoxy- or aryloxy-polyethylene glycol.

Pegylation of PCC proteins may be carried out by any of the pegylation reactions known in the art. Pegylation may be carried out via an acylation reaction or an alkylation reaction with a reactive polyethylene glycol molecule (or an analogous reactive water-soluble polymer) as described below. For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono $C_1$-$C_{10}$ alkoxy or aryloxy derivatives thereof.

In general, chemical derivatization may be performed under any suitable conditions used to react a biologically active substance with an activated polymer molecule. For example, methods for preparing PEGylated PCC proteins will generally comprise the steps of (a) reacting the protein with polyethylene glycol (such as a reactive ester, amine, aldehyde or maleimide derivative of PEG) under conditions whereby PCC protein becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-PEGylated product. In one particular aspect, the PCC protein derivative will have a single PEG moiety at the amino terminus. In particular embodiments, the PEGylated PCC protein enzyme provided by the invention has an average of about 1 to about 10, more particularly 2 to about 5 and more particularly 3 to 5 PEG molecules covalently attached to each PCC protein enzyme subunit in the composition.

Proteins of the present invention are preferably retrieved, obtained, and/or used in "substantially pure" form. As used herein, "substantially pure" refers to a purity that allows for the effective use of the protein in vitro, ex vivo or in vivo according to the present invention. For a protein to be useful in an in vitro, ex vivo or in vivo method according to the present invention, it is substantially free of contaminants, other proteins and/or chemicals that might interfere or that would interfere with its use in a method disclosed by the present invention, or that at least would be undesirable for inclusion with an PCC protein (including homologues) when it is used in a method disclosed by the present invention. Such methods include enzymatic reactions, preparation of therapeutic compositions, administration in a therapeutic composition, and all other methods disclosed herein. A "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (e.g., the PCC protein is about 80% of the protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition. In embodiments of the PCC protein or variants thereof produced in recombinant bacteria, the terms "purified" or "substantially pure" will be understood to encompass purification from lipopolysaccharides and other pyrogenic compounds.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of posttranslational modifications. Additionally, the promoter sequence might be genetically engineered to improve the level of expression as compared to the native promoter.

Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably any site where it is desirable to regulate PCC enzyme activity. Pharmaceutically acceptable carriers are capable of maintaining a protein or recombinant nucleic acid molecule of the present invention in a form that, upon arrival of the protein or recombinant nucleic acid molecule at the target cell or tissue in a culture or in patient, the protein or recombinant nucleic acid molecule is capable of interacting with its target (e.g., a substrate for PCC).

Suitable excipients of the present invention include excipients or formularies that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a compound of the present invention (e.g., a protein (including homologues), an antibody, a nucleic acid molecule, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphe res, and transdermal delivery systems. Other carriers of the present invention include liquids that, upon administration to a patient, form a solid or a gel in situ. In specific embodiments, carriers are also biodegradable bioerodible). When the compound is a recombinant nucleic acid molecule, suitable carriers include, but are not limited to liposomes, viral vectors or other carriers, including ribozymes, gold particles, poly-L-lysine/DNA-molecular conjugates, and artificial chromosomes. Natural lipid-containing carriers include cells and cellular membranes. Artificial lipid-containing carriers include liposomes and micelles.

A carrier of the present invention can be modified to target to a particular site in a patient, thereby targeting and making use of a protein of the present invention at that site. A pharmaceutically acceptable carrier that is capable of targeting can also be referred to herein as a "delivery vehicle" or "targeting carrier". Suitable modifications include manipulating the chemical formula of the lipid portion of the delivery vehicle and/or introducing into the vehicle a targeting agent capable of specifically targeting a delivery vehicle to a preferred site or target site, for example, a preferred cell type. A "target site" refers to a site in a patient to which one desires to deliver a composition. Alternatively, said pharmaceutically acceptable carriers can comprise agents suitable for delivering said PCC proteins to an animal, preferably a human, in blood plasma or serum. Suitable targeting compounds include cell penetrating peptides or ligands capable of selectively (i.e., specifically) binding another molecule at a particular site. Examples of cell penetrating peptides include homeodomain transcription factors such as Antennapedia (SEQ ID NO: 7), VP22 (SEQ ID NO: 8), TAT (SEQ ID NO: 5), penetratin (SEQ ID NO: 9), and transportan (SEQ ID NO: 10); ampiphatic such as MPG (SEQ ID NO: 11), Pep-1 (SEQ ID NO: 12), MAP (SEQ ID NO: 13), SAP (SEQ ID NO: 14) and PPTG1 (SEQ ID NO: 15); and other such as poly-Arginine sequences (SEQ ID NO: 16), hCT (SEQ ID NO: 17), SynB (SEQ ID NO: 18), and Pvec (SEQ ID NO: 19). Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In specific embodiments, liposomes of the present invention include those liposomes commonly used in, for example, protein delivery methods known to those of skill in the art. Complexing a liposome with a protein of the present invention can be achieved using methods standard in the art.

Methods well known to those skilled in the art can be used to construct expression vectors and recombinant bacterial cells according to this invention. These methods include in vitro recombinant DNA techniques, synthetic techniques, in vivo recombination techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and *PCR Protocols: A Guide to Methods and Applications* (Innis et al., 1990, Academic Press, San Diego, Calif.).

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or can not be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the terms "polynucleotide", "nucleotide", "oligonucleotide", and "nucleic acid" can be used interchangeably to refer to nucleic acid comprising DNA, RNA, derivatives thereof, or combinations thereof.

In various aspects of the invention provides a method for providing isolated human propionyl-CoA carboxylase (PCC) to a cell having a deficiency thereof wherein the PCC comprises one or both of an isolated propionyl-CoA carboxylase, alpha chain protein (PCCA) comprising the amino acid sequence of SEQ ID NO:2, and/or an isolated propionyl-CoA carboxylase, beta chain protein (PCCB) comprising the amino acid sequence of SEQ ID NO:4, wherein the method comprises the steps of contacting said cell with a preparation of the isolated human PCC at a concentration sufficient for the cell to take up a therapeutically effective amount of PCC, wherein the PCC deficiency in the cell is alleviated thereby.

In a further aspect, the invention provides a method for treating PCC deficiency in an individual in need thereof, comprising administering a therapeutically effective amount of a pharmaceutical composition of isolated human PCC to the individual in need thereof, wherein the isolated human PCC comprises one or both of an isolated propionyl-CoA carboxylase, alpha chain protein (PCCA) comprising the amino acid sequence of SEQ ID NO:2, and/or an isolated propionyl-CoA carboxylase, beta chain protein (PCCB) comprising the amino acid sequence of SEQ ID NO:4.

In yet another aspect, the invention provides pharmaceutical composition comprising a therapeutically effective amount of isolated human PCC wherein the PCC comprises one or both of an isolated propionyl-CoA carboxylase, alpha chain protein (PCCA) comprising the amino acid sequence of SEQ ID NO:2, and/or an isolated propionyl-CoA carboxylase, beta chain protein (PCCB) comprising the amino acid sequence of SEQ ID NO:4, and a pharmaceutically acceptable carrier, diluent or excipient.

In some embodiments, the pharmaceutical composition is administered by intravenous injection, subcutaneous injection, or intraperitoneal injection. The pharmaceutical composition may comprise an amount of PCC protein wherein 0.01 mg/kg-20 mg/kg is administered to an individual in need thereof.

In another embodiment, the invention provides a method for treating or ameliorating a disease, disorder, or condition, associated with elevated propionyl CoA, propionic acid, methylcitrate, beta-hydroxy-propionate, propionylglycine, tiglic acid, and ketones comprising administering to an individual in need thereof a pharmaceutically effective amount of a pharmaceutical composition of PCC. In one embodiment, the disease, disorder, or condition associated with elevated propionyl CoA, propionic acid, methylcitrate, beta-hydroxy-propionate, propionylglycine, tiglic acid, and ketones is poor feeding, vomiting, and somnolence, lethargy, seizures, coma, metabolic acidosis, anion gap, ketonuria, hypoglycemia, hyperammonemia, cytopenias, developmental regression, chronic vomiting, protein intolerance, failure to thrive, hypotonia, basal ganglia infarction, dystonia, choreoathetosis, and cardiomyopathy.

In certain embodiments, the invention provides a composition of matter comprising one or both of an isolated propionyl-CoA carboxylase, alpha chain protein (PCCA) comprising the amino acid sequence of SEQ ID NO:2, and/or an isolated propionyl-CoA carboxylase, beta chain protein (PCCB) comprising the amino acid sequence of SEQ ID NO:4.

In another aspect the PCCA protein and/or PCCB protein comprises a mitochondrial leader sequence. In another aspect the PCCA protein and/or PCCB protein lack a mitochondrial leader sequence. In various embodiments the PCCA protein and/or PCCB proteins are genetically engineered proteins or variant thereof.

In another embodiment the PCCA protein and/or PCCB protein is covalently linked to one or a plurality of cell penetrating peptides, a non-limiting example of such a cell penetration peptide is trans-activating transcriptional activator (TAT) or a tissue specific variant thereof (SEQ ID NO: 5, 6 and 20). In some embodiments the the cell-penetrating peptide is chemically added post-translation of the PCCA or PCCB peptide.

In certain embodiments, the PCCA and/or PCCB proteins are produced recombinantly. The PCCA and/or PCCB proteins may be produced in prokaryotic or eukaryotic cells, more specifically yeast, mammalian or *E. coli*.

In other embodiments, the PCCA and/or PCCB proteins are covalently linked to one or a plurality of polyethylene glycol molecules.

The methods and compositions of the disclosure can be used for a wide variety of pharmaceutical and medicinal purposes that are known in the art.

EXAMPLES

The Examples that follow are illustrative of specific embodiments of the invention, and various uses thereof. They are set forth for explanatory purposes only, and are not to be taken as limiting the invention.

Example 1: Construction of Expression Plasmids Comprising Propionyl-CoA Carboxylase (PCC)

Plasmid constructs were developed for expression of the propionyl-CoA carboxylase enzyme in E. coli, including the E. coli codon optimized construct encoding both mature PCC subunits (PCCA; SEQ ID NO:1; and PCCB; SEQ ID NO:3), individual PCC subunits with and without the mitochondrial targeting leader (mitochondrial leader sequences correspond to amino acids 1-21 of full-length PCCA protein and amino acids 1-31 of full-length PCCB protein), with and without a cell-penetrating peptide, such as trans-activating transcriptional activator (TAT) peptide (YGRKKRRQRRR; SEQ ID NO:5). The latter would be used for a subsequent covalent modification with a TAT peptide or for injection of a mixture of PCC and the TAT peptide.

TABLE 2

Examples of constructs for expression of PCC enzyme
Molecule expressed

PCCA

PCCA with or without a mitochondrial targeting leader sequence
PCCA with or without a mitochondrial targeting leader sequence with cell penetrating peptide
PCCA with or without a mitochondrial targeting leader sequence with post-translationally linked cell penetrating peptide

PCCB

PCCB with or without a mitochondrial targeting leader sequence
PCCB with or without a mitochondrial targeting leader sequence with cell penetrating peptide
PCCB with or without amitochondrial targeting leader sequence with post-translationally linked cell penetrating peptide

PCCA:PCCB

PCCA:PCCB with or without a mitochondrial targeting leader sequence
PCCA:PCCB with or without a mitochondrial targeting leader sequence with cell penetrating peptide
PCCA:PCCB with or without a mitochondrial targeting leader sequence with post-translationally linked cell penetrating peptide

Example 2: Expression and Purification of Human PCC

The recombinant human PCC expression construct designated pPCCAB produces PCC protein in E. coli (FIG. 1), and has been described in Kelson et al., 1996 Human Molecular Genetics. 5:331-37. This plasmid has been designed to facilitate the simultaneous and balanced expression of both PCCA and PCCB subunits in E. coli (see Kelson et al., 1996 Human Molecular Genetics. 5:331-37). Mature-length PCCA and PCCB cDNAs were constructed from the full-length cDNA clones by moving the translation start site downstream to the amino acid residue where the amino terminus of the mature enzyme was postulated to be. The pPCCAB expression plasmid was engineered so that the initiator methionine of the mature-length PCCA cDNA corresponded to amino acid residue 26 of the full-length precursor. Translation of the PCCA cDNA was driven by the tac promoter from the original PinPoint Xa vector. The PCCB cDNA was constructed so that the initiator methionine of the mature-length cDNA corresponded to amino acid residue 31 of the full-length precursor. Translation of PCCB was driven by a trc promoter from the pKK388.1 vector and this promoter and ribosomal binding site were ligated 20 bp upstream of the PCCB cDNA translational start site. Subsequent experiments have demonstrated that successful assembly of wild type PCC in E. coli is greatly aided by the presence of co-expressed molecular chaperonins GroES and GroEL (Kelson et al., 1996 Human Molecular Genetics. 5:331-37). Co-expression studies were performed by electroporating both pGroESL and pPCCAB into E. coli DH5a F'IQ cells. The pGroESL plasmid confers resistance to chloramphenicol. Doubly transformed cells were selected on LB media containing 50 mg/ml ampicillin and 50 mg/ml chloramphenicol. Bacterial cultures grown to confluence overnight were diluted 1/100 and used to inoculate 0.5 l aliquots of LB media which were grown with shaker aeration at 37° C. in the presence of ampicillin (300 mg/ml), chloramphenicol (30 mg/ml) and biotin (5 mM) to a turbidity of ~0.4 at 600 nm prior to induction with 1 mM IPTG (BRL). The induced cells were allowed to grow for 2-24 h before collection. Cells were harvested on ice, collected by centrifugation (10,000 g for 10 min) followed by one washing with phosphate-buffered saline (PBS) and resuspended in 100 mM Tris-HCl, pH 7.5, 1 mM EDTA, 0.1 mM DTT and 1 mg/ml lysozyme followed by stirring for 1 h at 4 C. The lysate was sonicated twice for 5 min each time at 50% duty with a power setting of 3-4 using a model W225 sonicator (Heat-Ultrasonics, Inc.). Cell lysates were cleared by centrifugation at 15,000 g for 15 min and the supernatant (soluble fraction) was collected. The pellet (insoluble fraction) was resuspended in the original volume of Laemmli sample buffer and dissolved by boiling for 5 min.

Bacterial crude extracts were loaded onto a DEAE DE52 column (5×12.5 cm) (Whatman) previously equilibrated with 10 mM potassium phosphate, pH 7.0. The column was washed with 10 mM potassium phosphate, pH 6.5, followed by 30 mM potassium phosphate, pH 6.5. PCC was eluted with 70 mM potassium phosphate, pH 6.5. The eluate was concentrated on Amicon using XM50 membranes (Millipore) and then adjusted with 10×PBS buffer to a final concentration of 1×PBS solution. This solution was loaded onto a monomeric avidin column (2.5×10 cm) (Pierce) previously equilibrated with PBS, pH 7.4. Recombinant PCC was incubated on the affinity column for 30 minutes and then eluted with 0.5 mM biotin in PBS, pH 7.4, after washing with PBS, pH 7.4. The protein was concentrated on Amicon with XM50 membranes to approximately 1-2 ml, and loaded onto a HR Sephacryl™ S-400 size exclusion column (1.5×95 cm) (Amersham Biosciences). One main protein peak was collected. There was a small but much broader peak after this main peak in some of the variants containing primarily free alpha subunit. The purity of the preparations was approximately 95% as judged by SDS-PAGE. The proteins were then stored at a final concentration of 5-10 mg/ml in 10 mM potassium phosphate, pH 6.5, or PBS, pH 7.4, at −80° C. (see Jiang et al., 2005 J Biol.Chem. 280(30):27719-27).

Example 3: Characterization and Modifications of Various Forms of PCC

Various forms or variants of PCC individual proteins are expressed, purified and characterized in terms of: 1) solubility, 2) ability to reconstitute active PCC enzyme activity, and 3) identification of protease sensitive sites. Individual PCC proteins are tested with subsequent changes of sites of interest by amino acid substitutions. Studies of nucleic acid and/or amino acid modifications or PCC chemical modifications that mask potential immunogenic epitopes on the surface of a protein and/or hinder access to the protein for proteolytic enzymes are of interest. Other modifications of interest include those that advantageously alter the physicochemical properties of the PCC peptide, thus modifying its biodistribution, stability, and solubility without significantly detracting from its potency. Further experiments test the effect of chemical modifications, such as pegylation, to deliver the proteins to cells, or additional experiments aimed at optimization of the TAT peptide sequence or other cell-penetrating peptides.

Example 4: Import of PCCA Precursor into Hamster CH Cells

The sequence encoding the precursor of the PCCA subunit was cloned into an expression plasmid preceded by the TAT peptide sequence. The expressed protein was reconstituted from the inclusion bodies and added to the MEM medium in which the hamster cells were grown on a microscope slide. The cells were fixed and stained with anti-PCCA antibody. Subsequently, a secondary fluorescent antibody was used. PCC presence was detected throughout the cells.

Example 5: Uptake of PCC

Uptake of various forms of PCC subunits, with and without mitochondrial leader peptides, and/or with and without cell-penetrating peptides are examined in: isolated rat liver mitochondria, human control samples, human PA patient derived cells, and in PA mouse models. Pharmacokinetic and pharmacodynamic characterization of the PCC uptake combined with monitoring of the toxic metabolites characteristic of PA disease are also studied.

Example 6: Import of Assembled PCC Dodecamer into Patient Fibroblasts—Covalent Attachment of TAT to Solvent Accessible Cysteine(s)

Maleoyl-beta-Ala-TAT (KeraFAST®) was tested with the purified α6β6 PCC from Example 2. Two PA patient fibroblast cell lines were transfected with the PCC TAT protein mixture and reproducibly demonstrated full restoration of enzymatic activity to enzymatic activity about ten times the activity of normal fibroblasts (FIG. 2).

Example 7: Staining of Imported PCC in Patient Cells

Pure PCC was linked to a FITC-labeled TAT peptide. The FITC-TAT-PCC was added to the medium and the experiment was carried out as described in Example 6. FIG. 3 demonstrates that FITC-TAT-PCC appears in the cells including the mitochondria.

Example 8: Decrease of Intracellular Toxic Metabolites Upon PCC Import

PCC imported into the cells as described in Example 6 demonstrated reproducibly that the diagnostic C3/C2 ratio (propionyl-/acetyl-carnitine) in cell extracts of the PCC-treated cells significantly decreased in comparison to untreated controls.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

REFERENCES

1. Carrillo-Carrasco, N. & Venditti, C. (2012) Propionic Acidemia, *Gene Reviews*.
2. Saudubray, J. M., Ogier, H., Bonnefont, J. P., Munnich, A., Lombes, A., Herve, F., Mitchel, G., The, B. P., Specola, N., Parvy, P. & et al. (1989) Clinical approach to inherited metabolic diseases in the neonatal period: a 20-year survey, *J Inherit Metab Dis*. 12, 25-41.
3. Chace, D. H., DiPerna, J. C., Kalas, T. A., Johnson, R. W. & Naylor, E. W. (2001) Rapid Diagnosis of Methylmalonic and Propionic Acidemias: Quantitative Tandem Mass Spectrometric Analysis of Propionylcarnitine in Filter-Paper Blood Specimens Obtained from Newborns., *Clinical Chemistry*. 47, 2040-2044.
4. Ravn, K., Chloupkova, M., Christensen, E., Brandt, N. J., Simonsen, H., Kraus, J. P., Nielsen, I. M., Skovby, F. & Schwartz, M. (2000) High incidence of propionic acidemia in greenland is due to a prevalent mutation, 1540insCCC, in the gene for the beta-subunit of propionyl CoA carboxylase, *Am J Hum Genet*. 67, 203-6.
5. Menkes, J. H. (1966) Idiopathic hyperglycinemia: isolation and identification of three previously undescribed urinary ketones, *The Journal of pediatrics*. 69, 413-21.
6. Coude, F. X., Sweetman, L. & Nyhan, W. L. (1979) Inhibition by propionyl-coenzyme A of N-acetylglutamate synthetase in rat liver mitochondria. A possible explanation for hyperammonemia in propionic and methylmalonic acidemia, *Journal of Clinical Investigation*. 64, 1544-51.
7. Stewart, P. M. & Walser, M. (1980) Failure of the normal ureagenic response to amino acids in organic acid-loaded rats. Proposed mechanism for the hyperammonemia of propionic and methylmalonic acidemia, *Journal of Clinical Investigation*. 66, 484-92.
8. Fenton, W. A., Gravel, R. A. & Rosenblatt, D. S. (2001) Disorders of propionate and methylmalonate metabolism in *The Metabolic and Molecular Bases of Inherited Disease* (Scriver, C. R., Beaudet, A. L., Sly, W. S. & Valle, D., eds) pp. 2165-2204, McGraw-Hill, Inc., New York.
9. Wolf, B., Hsia, Y. E., Sweetman, L., Gravel, R., Harris, D. J. & Nyhan, W. L. (1981) Propionic acidemia: a clinical update, *Journal of Pediatrics*. 99, 835-46.
10. Chloupkova, M., Ravn, K., Schwartz, M. & Kraus, J. P. (2000) Changes in the carboxyl terminus of the beta subunit of human propionyl-CoA carboxylase affect the oligomer assembly and catalysis: expression and characterization of seven patient-derived mutant forms of PCC in *Escherichia coli, Mol Genet Metab*. 71, 623-32.
11. Gravel, R. A., Lam, K. F., Mahuran, D. & Kronis, A. (1980) Purification of human liver propionyl-CoA carboxylase by carbon tetrachloride extraction and monomeric avidin affinity chromatography, *Archives of Biochemistry & Biophysics*. 201, 669-73.
12. Kalousek, F., Darigo, M. D. & Rosenberg, L. E. (1980) Isolation and characterization of propionyl-CoA carboxylase from normal human liver. Evidence for a protomeric tetramer of nonidentical subunits, *Journal of Biological Chemistry.* 255, 60-5.
13. Lamhonwah, A. M., Barankiewicz, T. J., Willard, H. F., Mahuran, D. J., Quan, F. & Gravel, R. A. (1986) Isolation of cDNA clones coding for the alpha and beta chains of human propionyl-CoA carboxylase: chromosomal assignments and DNA polymorphisms associated with PCCA and PCCB genes, *Proceedings of the National Academy of Sciences of the United States of America.* 83, 4864-8.
14. Kraus, J. P., Williamson, C. L., Firgaira, F. A., Yang-Feng, T. L., Munke, M., Francke, U. & Rosenberg, L. E. (1986) Cloning and screening with nanogram amounts of immunopurified mRNAs: cDNA cloning and chromosomal mapping of cystathionine beta-synthase and the beta subunit of propionyl-CoA carboxylase, *Proceedings of the National Academy of Sciences of the United States of America.* 83, 2047-51.
15. Kraus, J. P., Firgaira, F., Novotny, J., Kalousek, F., Williams, K. R., Williamson, C., Ohura, T. & Rosenberg, L. E. (1986) Coding sequence of the precursor of the beta subunit of rat propionyl-CoA carboxylase, *Proceedings of the National Academy of Sciences of the United States of America.* 83, 8049-53.
16. Lamhonwah, A. M., Mahuran, D. & Gravel, R. A. (1989) Human mitochondrial propionyl-CoA carboxylase: localization of the N-terminus of the pro- and mature alpha chains in the deduced primary sequence of a full-length cDNA, *Nucleic Acids Research.* 17, 4396.
17. Lamhonwah, A. M., Leclerc, D., Loyer, M., Clarizio, R. & Gravel, R. A. (1994) Correction of the metabolic defect in propionic acidemia fibroblasts by microinjection of a full-length cDNA or RNA transcript encoding the propionyl-CoA carboxylase beta subunit, *Genomics.* 19, 500-5.
18. Ohura, T., Narisawa, K. & Tada, K. (1993) Propionic acidaemia: sequence analysis of mutant mRNAs from Japanese beta subunit-deficient patients, *J Inherit Metab Dis.* 16, 863-7.
19. Browner, M. F., Taroni, F., Sztul, E. & Rosenberg, L. E. (1989) Sequence analysis, biogenesis, and mitochondrial import of the alpha-subunit of rat liver propionyl-CoA carboxylase [published erratum appears in J Biol Chem 1991 Mar. 5; 266(7):4660], *Journal of Biological Chemistry.* 264, 12680-5.
20. Lamhonwah, A. M., Quan, F. & Gravel, R. A. (1987) Sequence homology around the biotin-binding site of human propionyl-CoA carboxylase and pyruvate carboxylase, *Archives of Biochemistry & Biophysics.* 254, 631-6.
21. Leon-Del-Rio, A. & Gravel, R. A. (1994) Sequence requirements for the biotinylation of carboxyl-terminal fragments of human propionyl-CoA carboxylase alpha subunit expressed in *Escherichia coli, Journal of Biological Chemistry.* 269, 22964-8.
22. Kelson, T. L., Ohura, T. & Kraus, J. P. (1996) Chaperonin-mediated assembly of wild-type and mutant subunits of human propionyl-CoA carboxylase expressed in *Escherichia coli, Human Molecular Genetics.* 5, 331-337.
23. Fang et al., 2013 *PLOS ONE* 8(3):e57318.
24. Ruoslahti et al., 2009 *J Cell Biology* 188(6):759-68.
25. Foged & Nielsen, 2008 *Expert Opin. Drug Deliv.* 5(1): 105-17.
26. Treat et al., 2012 *ACS Macro Lett.* 1(1): 100-04.
27. Jiang et al., 2005 *J Biol. Chem.* 280(30):27719-27.

What is claimed is:

1. A method for providing isolated human propionyl-CoA carboxylase (PCC) to a cell having a deficiency thereof, said method comprising: contacting the deficient cell with a preparation, said preparation comprising isolated human PCC having both an isolated propionyl-CoA carboxylase, alpha chain protein (PCCA) comprising the amino acid sequence of SEQ ID NO:2, and an isolated propionyl-CoA carboxylase, beta chain protein (PCCB) comprising the amino acid sequence of SEQ ID NO:4, wherein the PCCA protein or the PCCB protein is covalently linked to one or more trans-activating transcriptional activator (TAT) peptides, the isolated human PCC of the preparation is present in a concentration sufficient for the cell to take up a therapeutically effective amount of isolated human PCC, thereby alleviating the isolated human PCC deficiency in the cell.

2. The method of claim 1, wherein the PCCA protein or the PCCB protein comprises a mitochondrial leader sequence.

3. The method of claim 1, wherein the PCCA protein or the PCCB protein lacks a mitochondrial leader sequence.

4. The method of claim 1, wherein the PCCA protein or the PCCB protein is a genetically engineered protein.

5. The method of any of claim 1, wherein the PCCA protein or the PCCB protein is covalently linked to one or a plurality of polyethylene glycol molecules.

6. A method for treating PCC deficiency in an individual in need thereof, the method comprising administering to the individual in need thereof a therapeutically effective amount of a pharmaceutical composition comprising an isolated human PCC having both an isolated propionyl-CoA carboxylase, alpha chain protein (PCCA) comprising the amino acid sequence of SEQ ID NO:2, and an isolated propionyl-CoA carboxylase, beta chain protein (PCCB) comprising the amino acid sequence of SEQ ID NO:4, wherein the PCCA protein or the PCCB protein is covalently linked to one or a plurality of trans-activating transcriptional activator (TAT) peptides.

7. The method of claim 6, wherein the PCCA protein or the PCCB protein comprises a mitochondrial leader sequence.

8. The method of claim 6, wherein the PCCA protein or the PCCB protein lacks a mitochondrial leader sequence.

9. The method of claim 6, wherein the PCCA protein or the PCCB protein is a genetically engineered protein.

10. The method of claim 6, wherein the PCCA protein or the PCCB protein is covalently linked to one or a plurality of polyethylene glycol molecules.

* * * * *

SEQUENCE LISTING

```
<160> NUMBER OF SEQ ID NOS: 20

<210> SEQ ID NO 1
<211> LENGTH: 2577
<212> TYPE: DNA
<213> ORGANISM: Homo sapiens

<400> SEQUENCE: 1
ggcatcgggt ttctggctcg tgatttgccg gagctcctgc gctcccttc  tccaccccct      60 ccggctgtgt gagaggtcag cagaggggcg gtctgcgggg acaacaatgg cggggttctg     120
ggtcgggaca gcaccgctgg tcgctgccgg acggcgtggg cggtggccgc cgcagcagct     180
gatgctgagc gcggcgctgc ggaccctgaa gcatgttctg tactattcaa gacagtgctt     240
aatggtgtcc cgtaatcttg gttcagtggg atatgatcct aatgaaaaaa cttttgataa     300
aattcttgtt gctaatagag gagaaattgc atgtcgggtt attagaactt gcaagaagat     360
gggcattaag acagttgcca tccacagtga tgttgatgct agttctgttc atgtgaaaat     420
ggcggatgag gctgtctgtg ttggcccagc tcccaccagt aaaagctacc tcaacatgga     480
tgccatcatg gaagccatta agaaaccag  ggcccaagct gtacatccag gttatggatt     540
cctttcagaa aacaaagaat ttgccagatg tttggcagca gaagatgtcg ttttcattgg     600
acctgacaca catgctattc aagccatggg cgacaagatt gaaagcaaat tattagctaa     660
gaaagcagag gttaatacaa tccctggctt tgatggagta gtcaaggatg cagaagaagc     720
tgtcagaatt gcaagggaaa ttggctaccc tgtcatgatc aaggcctcag caggtggtgg     780
tgggaaaggc atgcgcattg cttgggatga tgaagagacc agggatggtt ttagattgtc     840
```

```
atctcaagaa gctgcttcta gttttggcga tgatagacta ctaatagaaa aatttattga      900
taatcctcgt catatagaaa tccaggttct aggtgataaa catgggaatg ctttatggct      960
taatgaaaga gagtgctcaa ttcagagaag aaatcagaag gtggtggagg aagcaccaag     1020
cattttttg gatgcggaga ctcgaagagc gatgggagaa caagctgtag ctcttgccag     1080
agcagtaaaa tattcctctg ctgggaccgt ggagttcctt gtggactcta agaagaattt     1140
ttatttcttg gaaatgaata caagactcca ggttgagcat cctgtcacag aatgcattac     1200
tggcctggac ctagtccagg aaatgatccg tgttgctaag ggctaccctc tcaggcacaa     1260
acaagctgat attcgcatca acggctgggc agttgaatgt cgggtttatg ctgaggaccc     1320
ctacaagtct tttggtttac catctattgg gagattgtct cagtaccaag aaccgttaca     1380
tctacctggt gtccgagtgg acagtggcat ccaaccagga agtgatatta gcatttatta     1440
tgatcctatg atttcaaaac taatcacata tggctctgat agaactgagg cactgaagag     1500
aatggcagat gcactggata ctatgttat tcgaggtgtt acacataata ttgcattact     1560
tcgagaggtg ataatcaact cacgctttgt aaaaggagac atcagcacta aatttctctc     1620
cgatgtgtat cctgatggct tcaaaggaca catgctaacc aagagtgaga agaaccagtt     1680
attggcaata gcatcatcat tgtttgtggc attccagtta agagcacaac attttcaaga     1740
aaattcaaga atgcctgtta ttaaaccaga catagccaac tgggagctct cagtaaaatt     1800
gcatgataaa gttcataccg tagtagcatc aaacaatggg tcagtgttct cggtggaagt     1860
tgatgggtcg aaactaaatg tgaccagcac gtggaacctg gcttcgccct tattgtctgt     1920
cagcgttgat ggcactcaga ggactgtcca gtgtctttct cgagaagcag gtggaaacat     1980
gagcattcag tttcttggta cagtgtacaa ggtgaatatc ttaaccagac ttgccgcaga     2040
attgaacaaa tttatgctgg aaaaagtgac tgaggacaca agcagtgttc tgcgttcccc     2100
gatgcccgga gtggtggtgg ccgtctctgt caagcctgga gacgcggtag cagaaggtca     2160
agaaatttgt gtgattgaag ccatgaaaat gcagaatagt atgacagctg ggaaaactgg     2220
cacggtgaaa tctgtgcact gtcaagctgg agacacagtt ggagaagggg atctgctcgt     2280
ggagctggaa tgaaggattt ataacctttc agtcatcacc caatttaatt agccatttgc     2340
atgatgcttt cacacacaat tgattcaagc attatacagg aacacccctg tgcagctacg     2400
tttacgtcgt catttattcc acagagtcaa gaccaatatt ctgccaaaaa atcaccaatg     2460
gaaattttca ttgatataaa tacttgtaca tatgatttgt acttctgctg tgagattccc     2520
tagtgtcaaa attaaatcaa taaaactgag catttgtcta ataaaaaaaa aaaaaaa      2577
```

<210> SEQ ID NO 2
<211> LENGTH: 728
<212> TYPE: PRT
<213> ORGANISM: Homo sapiens

<400> SEQUENCE: 2

Met Ala Gly Phe Trp Val Gly Thr Ala Pro Leu Val Ala Ala Gly Arg
1               5                   10                  15

Arg Gly Arg Trp Pro Pro Gln Gln Leu Met Leu Ser Ala Ala Leu Arg
            20                  25                  30

Thr Leu Lys His Val Leu Tyr Tyr Ser Arg Gln Cys Leu Met Val Ser
        35                  40                  45

Arg Asn Leu Gly Ser Val Gly Tyr Asp Pro Asn Glu Lys Thr Phe Asp
    50                  55                  60

Lys Ile Leu Val Ala Asn Arg Gly Glu Ile Ala Cys Arg Val Ile Arg

```
            65                  70                  75                  80
        Thr Cys Lys Lys Met Gly Ile Lys Thr Val Ala Ile His Ser Asp Val
                        85                  90                  95
        Asp Ala Ser Ser Val His Val Lys Met Ala Asp Glu Ala Val Cys Val
                        100                 105                 110
        Gly Pro Ala Pro Thr Ser Lys Ser Tyr Leu Asn Met Asp Ala Ile Met
                        115                 120                 125
        Glu Ala Ile Lys Lys Thr Arg Ala Gln Ala Val His Pro Gly Tyr Gly
                        130                 135                 140
        Phe Leu Ser Glu Asn Lys Glu Phe Ala Arg Cys Leu Ala Ala Glu Asp
        145                 150                 155                 160
        Val Val Phe Ile Gly Pro Asp Thr His Ala Ile Gln Ala Met Gly Asp
                        165                 170                 175
        Lys Ile Glu Ser Lys Leu Leu Ala Lys Ala Glu Val Asn Thr Ile
                        180                 185                 190
        Pro Gly Phe Asp Gly Val Val Lys Asp Ala Glu Ala Val Arg Ile
                        195                 200                 205
        Ala Arg Glu Ile Gly Tyr Pro Val Met Ile Lys Ala Ser Ala Gly Gly
                        210                 215                 220
        Gly Gly Lys Gly Met Arg Ile Ala Trp Asp Glu Glu Thr Arg Asp
        225                 230                 235                 240
        Gly Phe Arg Leu Ser Ser Gln Glu Ala Ala Ser Ser Phe Gly Asp Asp
                        245                 250                 255
        Arg Leu Leu Ile Glu Lys Phe Ile Asp Asn Pro Arg His Ile Glu Ile
                        260                 265                 270
        Gln Val Leu Gly Asp Lys His Gly Asn Ala Leu Trp Leu Asn Glu Arg
                        275                 280                 285
        Glu Cys Ser Ile Gln Arg Arg Asn Gln Lys Val Val Glu Glu Ala Pro
                        290                 295                 300
        Ser Ile Phe Leu Asp Ala Glu Thr Arg Arg Ala Met Gly Glu Gln Ala
        305                 310                 315                 320
        Val Ala Leu Ala Arg Ala Val Lys Tyr Ser Ser Ala Gly Thr Val Glu
                        325                 330                 335
        Phe Leu Val Asp Ser Lys Lys Asn Phe Tyr Phe Leu Glu Met Asn Thr
                        340                 345                 350
        Arg Leu Gln Val Glu His Pro Val Thr Glu Cys Ile Thr Gly Leu Asp
                        355                 360                 365
        Leu Val Gln Glu Met Ile Arg Val Ala Lys Gly Tyr Pro Leu Arg His
                        370                 375                 380
        Lys Gln Ala Asp Ile Arg Ile Asn Gly Trp Ala Val Glu Cys Arg Val
        385                 390                 395                 400
        Tyr Ala Glu Asp Pro Tyr Lys Ser Phe Gly Leu Pro Ser Ile Gly Arg
                        405                 410                 415
        Leu Ser Gln Tyr Gln Glu Pro Leu His Leu Pro Gly Val Arg Val Asp
                        420                 425                 430
        Ser Gly Ile Gln Pro Gly Ser Asp Ile Ser Ile Tyr Tyr Asp Pro Met
                        435                 440                 445
        Ile Ser Lys Leu Ile Thr Tyr Gly Ser Asp Arg Thr Glu Ala Leu Lys
                        450                 455                 460
        Arg Met Ala Asp Ala Leu Asp Asn Tyr Val Ile Arg Gly Val Thr His
        465                 470                 475                 480
        Asn Ile Ala Leu Leu Arg Glu Val Ile Ile Asn Ser Arg Phe Val Lys
                        485                 490                 495
```

Gly Asp Ile Ser Thr Lys Phe Leu Ser Asp Val Tyr Pro Asp Gly Phe
              500                 505                 510

Lys Gly His Met Leu Thr Lys Ser Glu Lys Asn Gln Leu Leu Ala Ile
              515                 520                 525

Ala Ser Ser Leu Phe Val Ala Phe Gln Leu Arg Ala Gln His Phe Gln
          530                 535                 540

Glu Asn Ser Arg Met Pro Val Ile Lys Pro Asp Ile Ala Asn Trp Glu
545                 550                 555                 560

Leu Ser Val Lys Leu His Asp Lys Val His Thr Val Ala Ser Asn
              565                 570                 575

Asn Gly Ser Val Phe Ser Val Glu Val Asp Gly Ser Lys Leu Asn Val
              580                 585                 590

Thr Ser Thr Trp Asn Leu Ala Ser Pro Leu Leu Ser Val Ser Val Asp
          595                 600                 605

Gly Thr Gln Arg Thr Val Gln Cys Leu Ser Arg Glu Ala Gly Gly Asn
          610                 615                 620

Met Ser Ile Gln Phe Leu Gly Thr Val Tyr Lys Val Asn Ile Leu Thr
625                 630                 635                 640

Arg Leu Ala Ala Glu Leu Asn Lys Phe Met Leu Glu Lys Val Thr Glu
              645                 650                 655

Asp Thr Ser Ser Val Leu Arg Ser Pro Met Pro Gly Val Val Val Ala
              660                 665                 670

Val Ser Val Lys Pro Gly Asp Ala Val Ala Glu Gly Gln Glu Ile Cys
          675                 680                 685

Val Ile Glu Ala Met Lys Met Gln Asn Ser Met Thr Ala Gly Lys Thr
690                 695                 700

Gly Thr Val Lys Ser Val His Cys Gln Ala Gly Asp Thr Val Gly Glu
705                 710                 715                 720

Gly Asp Leu Leu Val Glu Leu Glu
              725

<210> SEQ ID NO 3
<211> LENGTH: 1825
<212> TYPE: DNA
<213> ORGANISM: Homo sapiens

<400> SEQUENCE: 3

```
agcacatgcg tactcaggtg cgccggtagg ggacgcgccg gcacagcaaa aatggcggcg      60
gcattacggg tggcggcggt cggggcaagg ctcagcgttc tggcgagcgg tctccgcgcc     120
gcggtccgca gcctttgcag ccaggccacc tctgttaacg aacgcatcga aaacaagcgc     180
cggaccgcgc tgctgggagg gggccaacgc cgtattgacg cgcagcacaa gcgaggaaag     240
ctaacagcca gggagaggat cagtctcttg ctggaccctg gcagctttgt tgagagcgac     300
atgtttgtgg aacacagatg tgcagatttt ggaatggctg ctgataagaa taagtttcct     360
ggagacagcg tggtcactgg acgaggccga atcaatggaa gattggttta tgtcttcagt     420
caggatttta cagtttttgg aggcagtctg tcaggagcac atgcccaaaa gatctgcaaa     480
atcatggacc aggccataac ggtgggggct ccagtgattg gctgaatga ctctggggga     540 gcacggatcc aagaaggagt ggagtctttg gctggctatg cagacatctt tctgaggaat     600
gttacggcat ccggagtcat ccctcagatt tctctgatca tgggcccatg tgctggtggg     660
gccgtctact ccccagccct aacagacttc acgttcatgg taaaggacac ctcctacctg     720
ttcatcactg gccctgatgt tgtgaagtct gtcaccaatg aggatgttac ccaggaggag     780
```

```
ctcggtggtg ccaagaccca caccaccatg tcaggtgtgg cccacagagc ttttgaaaat    840
gatgttgatg ccttgtgtaa tctccgggat ttcttcaact acctgcccct gagcagtcag    900
gacccggctc ccgtccgtga gtgccacgat cccagtgacc gtctggttcc tgagcttgac    960
acaattgtcc ctttggaatc aaccaaagcc tacaacatgg tggacatcat acactctgtt   1020
gttgatgagc gtgaattttt tgagatcatg cccaattatg ccaagaacat cattgttggt   1080
tttgcaagaa tgaatgggag gactgttgga attgttggca accaacctaa ggtggcctca   1140
ggatgcttgg atattaattc atctgtgaaa ggggctcgtt ttgtcagatt ctgtgatgca   1200
ttcaatattc cactcatcac tttgttgat gtccctggct ttctacctgg cacagcacag   1260
gaatacgggg gcatcatccg gcatggtgcc aagcttctct acgcatttgc tgaggcaact   1320
gtacccaaag tcacagtcat caccaggaag gcctatggag gtgcctatga tgtcatgagc   1380
tctaagcacc tttgtggtga taccaactat gcctggccca ccgcagagat tgcagtcatg   1440
ggagcaaagg gcgctgtgga gatcatcttc aaagggcatg agaatgtgga agctgctcag   1500
gcagagtaca tcgagaagtt tgccaaccct ttccctgcag cagtgcgagg gtttgtggat   1560
gacatcatcc aaccttcttc cacacgtgcc cgaatctgct gtgacctgga tgtcttggcc   1620
agcaagaagg tacaacgtcc ttggagaaaa catgcaaata ttccattgta aacaaatcaa   1680
aggaaaagaa accaagaact gaattactgt ctgcccattc acatcccatt cctgcctttt   1740
gcaatcatga aacctgggaa tccaaatagt tggataactt agaataacta agtttattaa   1800
attctagaaa gatctcaaaa aaaaa                                         1825
```

<210> SEQ ID NO 4
<211> LENGTH: 539
<212> TYPE: PRT
<213> ORGANISM: Homo sapiens

<400> SEQUENCE: 4

```
Met Ala Ala Ala Leu Arg Val Ala Ala Val Gly Ala Arg Leu Ser Val
1               5                   10                  15

Leu Ala Ser Gly Leu Arg Ala Ala Val Arg Ser Leu Cys Ser Gln Ala
            20                  25                  30

Thr Ser Val Asn Glu Arg Ile Glu Asn Lys Arg Thr Ala Leu Leu
        35                  40                  45

Gly Gly Gly Gln Arg Arg Ile Asp Ala Gln His Lys Arg Gly Lys Leu
    50                  55                  60

Thr Ala Arg Glu Arg Ile Ser Leu Leu Leu Asp Pro Gly Ser Phe Val
65                  70                  75                  80

Glu Ser Asp Met Phe Val Glu His Arg Cys Ala Asp Phe Gly Met Ala
                85                  90                  95

Ala Asp Lys Asn Lys Phe Pro Gly Asp Ser Val Val Thr Gly Arg Gly
            100                 105                 110

Arg Ile Asn Gly Arg Leu Val Tyr Val Phe Ser Gln Asp Phe Thr Val
        115                 120                 125

Phe Gly Gly Ser Leu Ser Gly Ala His Ala Gln Lys Ile Cys Lys Ile
    130                 135                 140

Met Asp Gln Ala Ile Thr Val Gly Ala Pro Ile Gly Leu Asn Asp
145                 150                 155                 160

Ser Gly Gly Ala Arg Ile Gln Glu Gly Val Glu Ser Leu Ala Gly Tyr
                165                 170                 175

Ala Asp Ile Phe Leu Arg Asn Val Thr Ala Ser Gly Val Ile Pro Gln
```

```
                180             185             190
Ile Ser Leu Ile Met Gly Pro Cys Ala Gly Gly Ala Val Tyr Ser Pro
        195                 200                 205

Ala Leu Thr Asp Phe Thr Phe Met Val Lys Asp Thr Ser Tyr Leu Phe
        210                 215                 220

Ile Thr Gly Pro Asp Val Val Lys Ser Val Thr Asn Glu Asp Val Thr
225                 230                 235                 240

Gln Glu Glu Leu Gly Gly Ala Lys Thr His Thr Thr Met Ser Gly Val
                245                 250                 255

Ala His Arg Ala Phe Glu Asn Asp Val Asp Ala Leu Cys Asn Leu Arg
            260                 265                 270

Asp Phe Phe Asn Tyr Leu Pro Leu Ser Ser Gln Asp Pro Ala Pro Val
        275                 280                 285

Arg Glu Cys His Asp Pro Ser Asp Arg Leu Val Pro Glu Leu Asp Thr
        290                 295                 300

Ile Val Pro Leu Glu Ser Thr Lys Ala Tyr Asn Met Val Asp Ile Ile
305                 310                 315                 320

His Ser Val Val Asp Glu Arg Glu Phe Phe Glu Ile Met Pro Asn Tyr
                325                 330                 335

Ala Lys Asn Ile Ile Val Gly Phe Ala Arg Met Asn Gly Arg Thr Val
            340                 345                 350

Gly Ile Val Gly Asn Gln Pro Lys Val Ala Ser Gly Cys Leu Asp Ile
        355                 360                 365

Asn Ser Ser Val Lys Gly Ala Arg Phe Val Arg Phe Cys Asp Ala Phe
        370                 375                 380

Asn Ile Pro Leu Ile Thr Phe Val Asp Val Pro Gly Phe Leu Pro Gly
385                 390                 395                 400

Thr Ala Gln Glu Tyr Gly Gly Ile Ile Arg His Gly Ala Lys Leu Leu
                405                 410                 415

Tyr Ala Phe Ala Glu Ala Thr Val Pro Lys Val Thr Val Ile Thr Arg
            420                 425                 430

Lys Ala Tyr Gly Gly Ala Tyr Asp Val Met Ser Ser Lys His Leu Cys
        435                 440                 445

Gly Asp Thr Asn Tyr Ala Trp Pro Thr Ala Glu Ile Ala Val Met Gly
        450                 455                 460

Ala Lys Gly Ala Val Glu Ile Ile Phe Lys Gly His Glu Asn Val Glu
465                 470                 475                 480

Ala Ala Gln Ala Glu Tyr Ile Glu Lys Phe Ala Asn Pro Phe Pro Ala
                485                 490                 495

Ala Val Arg Gly Phe Val Asp Asp Ile Ile Gln Pro Ser Ser Thr Arg
            500                 505                 510

Ala Arg Ile Cys Cys Asp Leu Asp Val Leu Ala Ser Lys Lys Val Gln
        515                 520                 525

Arg Pro Trp Arg Lys His Ala Asn Ile Pro Leu
        530                 535

<210> SEQ ID NO 5
<211> LENGTH: 11
<212> TYPE: PRT
<213> ORGANISM: Artificial sequence
<220> FEATURE:
<223> OTHER INFORMATION: Description of Artificial Sequence: Cell
      penetrating protein, HIV-1 trans-activating transcriptional
      activator (TAT) peptide variant

<400> SEQUENCE: 5
```

-continued

```
Tyr Gly Arg Lys Lys Arg Arg Gln Arg Arg Arg
1               5                   10
```

<210> SEQ ID NO 6
<211> LENGTH: 12
<212> TYPE: PRT
<213> ORGANISM: Artificial sequence
<220> FEATURE:
<223> OTHER INFORMATION: Description of Artificial Sequence: Cell
      penetrating protein, HIV-1 trans-activating transcriptional
      activator (TAT) peptide variant

<400> SEQUENCE: 6

```
Gly Arg Lys Lys Arg Arg Gln Arg Arg Arg Pro Gln
1               5                   10
```

<210> SEQ ID NO 7
<211> LENGTH: 16
<212> TYPE: PRT
<213> ORGANISM: Artificial sequence
<220> FEATURE:
<223> OTHER INFORMATION: Description of Artificial Sequence: Cell
      penetrating protein, homeodomain transcription factor

<400> SEQUENCE: 7

```
Arg Gln Ile Lys Ile Tyr Phe Gln Asn Arg Arg Met Lys Trp Lys Lys
1               5                   10                  15
```

<210> SEQ ID NO 8
<211> LENGTH: 34
<212> TYPE: PRT
<213> ORGANISM: Artificial sequence
<220> FEATURE:
<223> OTHER INFORMATION: Description of Artificial Sequence: Cell
      penetrating protein, homeodomain transcription factor

<400> SEQUENCE: 8

```
Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp
```

<210> SEQ ID NO 9
<211> LENGTH: 16
<212> TYPE: PRT
<213> ORGANISM: Artificial sequence
<220> FEATURE:
<223> OTHER INFORMATION: Description of Artificial Sequence: Cell
      penetrating protein, homeodomain transcription factor

<400> SEQUENCE: 9

```
Arg Gln Ile Lys Ile Trp Phe Gln Asn Arg Arg Met Lys Trp Lys Lys
1               5                   10                  15
```

<210> SEQ ID NO 10
<211> LENGTH: 27
<212> TYPE: PRT
<213> ORGANISM: Artificial sequence
<220> FEATURE:
<223> OTHER INFORMATION: Description of Artificial Sequence: Cell
      penetrating protein, homeodomain transcription factor

<400> SEQUENCE: 10

```
Gly Trp Thr Leu Asn Ser Ala Gly Tyr Leu Leu Gly Lys Ile Asn Leu
1               5                   10                  15
```

```
Lys Ala Leu Ala Ala Leu Ala Lys Lys Ile Leu
            20                  25

<210> SEQ ID NO 11
<211> LENGTH: 27
<212> TYPE: PRT
<213> ORGANISM: Artificial sequence
<220> FEATURE:
<223> OTHER INFORMATION: Description of Artificial Sequence: Cell
      penetrating protein, ampiphatic protein

<400> SEQUENCE: 11

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 12
<211> LENGTH: 21
<212> TYPE: PRT
<213> ORGANISM: Artificial sequence
<220> FEATURE:
<223> OTHER INFORMATION: Description of Artificial Sequence: Cell
      penetrating protein, ampiphatic protein

<400> SEQUENCE: 12

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 13
<211> LENGTH: 12
<212> TYPE: PRT
<213> ORGANISM: Artificial sequence
<220> FEATURE:
<223> OTHER INFORMATION: Description of Artificial Sequence: Cell
      penetrating protein, ampiphatic protein

<400> SEQUENCE: 13

Lys Ala Leu Ala Lys Ala Leu Ala Lys Ala Leu Ala
1               5                   10

<210> SEQ ID NO 14
<211> LENGTH: 18
<212> TYPE: PRT
<213> ORGANISM: Artificial sequence
<220> FEATURE:
<223> OTHER INFORMATION: Description of Artificial Sequence: Cell
      penetrating protein, ampiphatic protein

<400> SEQUENCE: 14

Val Arg Leu Pro Pro Pro Val Arg Leu Pro Pro Pro Val Arg Leu Pro
1               5                   10                  15

Pro Pro

<210> SEQ ID NO 15
<211> LENGTH: 20
<212> TYPE: PRT
<213> ORGANISM: Artificial sequence
<220> FEATURE:
<223> OTHER INFORMATION: Description of Artificial Sequence: Cell
      penetrating protein

<400> SEQUENCE: 15
```

```
Gly Leu Phe Arg Ala Leu Leu Arg Leu Leu Arg Ser Leu Trp Arg Leu
1               5                   10                  15

Leu Leu Arg Ala
            20

<210> SEQ ID NO 16
<211> LENGTH: 8
<212> TYPE: PRT
<213> ORGANISM: Artificial sequence
<220> FEATURE:
<223> OTHER INFORMATION: Description of Artificial Sequence: Cell
      penetrating protein

<400> SEQUENCE: 16

Arg Arg Arg Arg Arg Arg Arg Arg
1               5

<210> SEQ ID NO 17
<211> LENGTH: 22
<212> TYPE: PRT
<213> ORGANISM: Artificial sequence
<220> FEATURE:
<223> OTHER INFORMATION: Description of Artificial Sequence: Cell
      penetrating protein

<400> SEQUENCE: 17

Leu Gly Thr Tyr Thr Gln Asp Phe Asn Lys Thr Phe Pro Gln Thr Ala
1               5                   10                  15

Ile Gly Val Gly Ala Pro
            20

<210> SEQ ID NO 18
<211> LENGTH: 18
<212> TYPE: PRT
<213> ORGANISM: Artificial sequence
<220> FEATURE:
<223> OTHER INFORMATION: Description of Artificial Sequence: Cell
      penetrating protein

<400> SEQUENCE: 18

Arg Gly Gly Arg Leu Ser Tyr Ser Arg Arg Phe Ser Thr Ser Thr
1               5                   10                  15

Gly Arg

<210> SEQ ID NO 19
<211> LENGTH: 18
<212> TYPE: PRT
<213> ORGANISM: Artificial sequence
<220> FEATURE:
<223> OTHER INFORMATION: Description of Artificial Sequence: Cell
      penetrating protein

<400> SEQUENCE: 19

Leu Leu Ile Ile Leu Arg Arg Arg Ile Arg Lys Gln Ala His Ala His
1               5                   10                  15

Ser Lys

<210> SEQ ID NO 20
<211> LENGTH: 36
<212> TYPE: PRT
<213> ORGANISM: Artificial sequence
<220> FEATURE:
<223> OTHER INFORMATION: Description of Artificial Sequence: Cell
      penetrating protein, HIV-1 trans-activating transcriptional
      activator (TAT) peptide variant
```

```
<400> SEQUENCE: 20

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
            35
```